(12) United States Patent
Alford et al.

(10) Patent No.: US 12,064,208 B2
(45) Date of Patent: *Aug. 20, 2024

(54) TIME-OF-FLIGHT OPTICAL MEASUREMENT AND DECODING OF FAST-OPTICAL SIGNALS

(71) Applicant: HI LLC, Los Angeles, CA (US)

(72) Inventors: Jamu Alford, Simi Valley, CA (US); Adam Marblestone, Arlington, MA (US); Ivo Vellekoop, Enschede (NL); Daniel Sobek, Portola Valley, CA (US); Michael Henninger, Austin, TX (US); Brian Robinson, Ellicott City, MD (US); Yuecheng Shen, Guangzhou University (CN); Roarke Horstmeyer, Durham, NC (US)

(73) Assignee: HI LLC, Los Angeles, CA (US)

( * ) Notice: Subject to any disclaimer, the term of this patent is extended or adjusted under 35 U.S.C. 154(b) by 84 days.

This patent is subject to a terminal disclaimer.

(21) Appl. No.: 17/663,992

(22) Filed: May 18, 2022

(65) Prior Publication Data

US 2023/0301515 A1   Sep. 28, 2023

Related U.S. Application Data

(63) Continuation of application No. 16/533,133, filed on Aug. 6, 2019, now Pat. No. 11,412,930.

(60) Provisional application No. 62/722,152, filed on Aug. 23, 2018.

(51) Int. Cl.
*A61B 5/00* (2006.01)
*A61B 5/026* (2006.01)

(52) U.S. Cl.
CPC .......... *A61B 5/0004* (2013.01); *A61B 5/0066* (2013.01); *A61B 5/0084* (2013.01); *A61B 5/0261* (2013.01)

(58) Field of Classification Search
None
See application file for complete search history.

(56) References Cited

PUBLICATIONS

Okada et al. ("A computationally efficient filter for reducing shot noise in low S/N data" (Year: 2016).*

* cited by examiner

*Primary Examiner* — Patrick Fernandes
*Assistant Examiner* — Marjan Saboktakin
(74) *Attorney, Agent, or Firm* — Michael J. Bolan; Vista IP Law Group, LLP

(57) ABSTRACT

An optical measurement system comprising an optical source configured for delivering sample light in an anatomical structure, such that the sample light is scattered by the anatomical structure, resulting in physiological-encoded signal light that exits the anatomical structure, an optical detector configured for detecting the physiological-encoded signal light, and a processor configured for acquiring a TOF profile derived from the physiological-encoded signal light, the initial TOF profile having an initial contrast-to-noise ratio (CNR) between a plurality of states of a physiological activity in the anatomical structure. The processor is further configured for applying one or more weighting functions to the initial TOF profile to generate a weighted TOF profile having a subsequent CNR greater than the initial CNR between the plurality of states of the physiological activity. The processor is further configured for processing the weighted TOF profile, and identifying one of the plurality of states of the physiological activity.

16 Claims, 20 Drawing Sheets

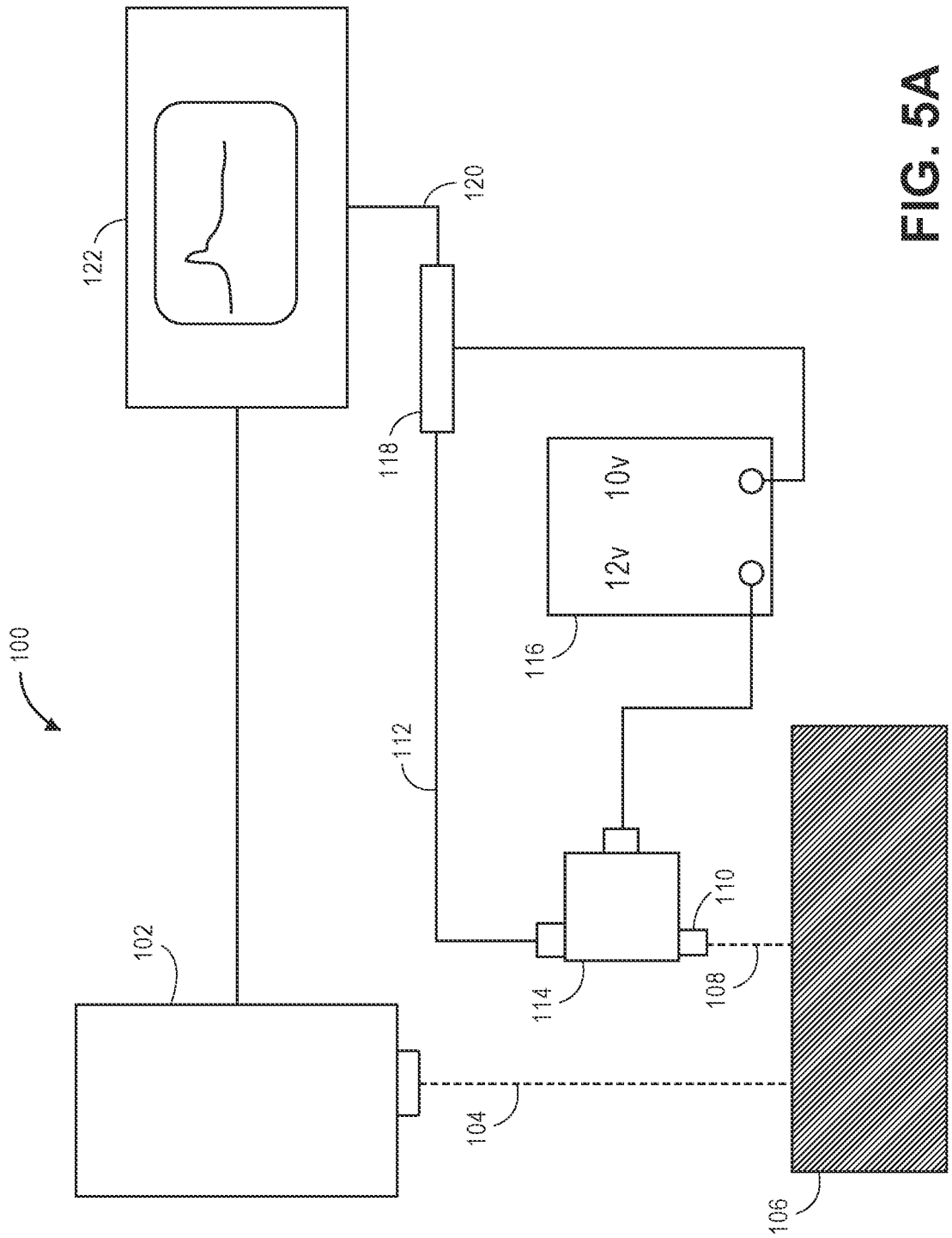

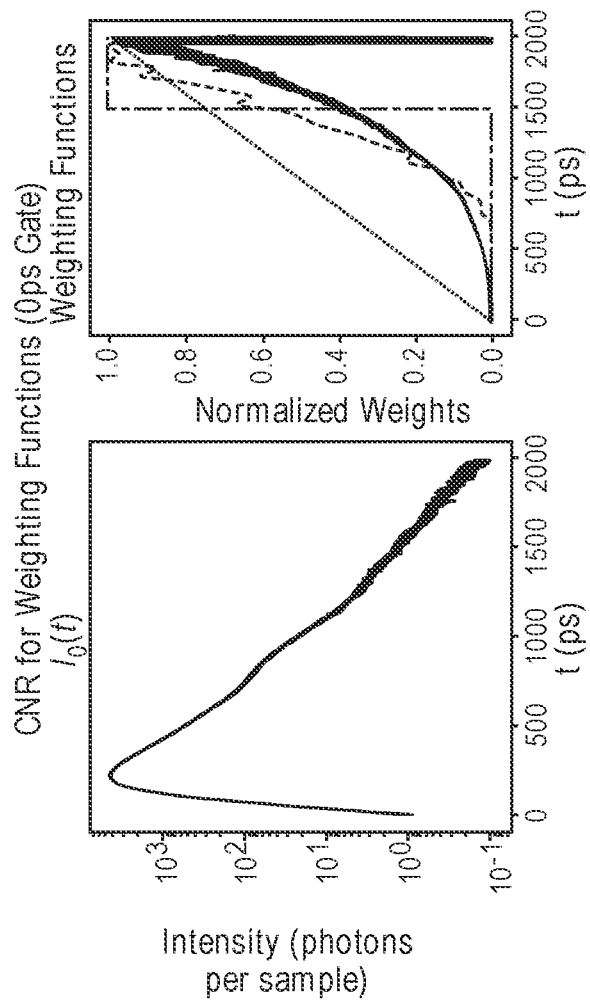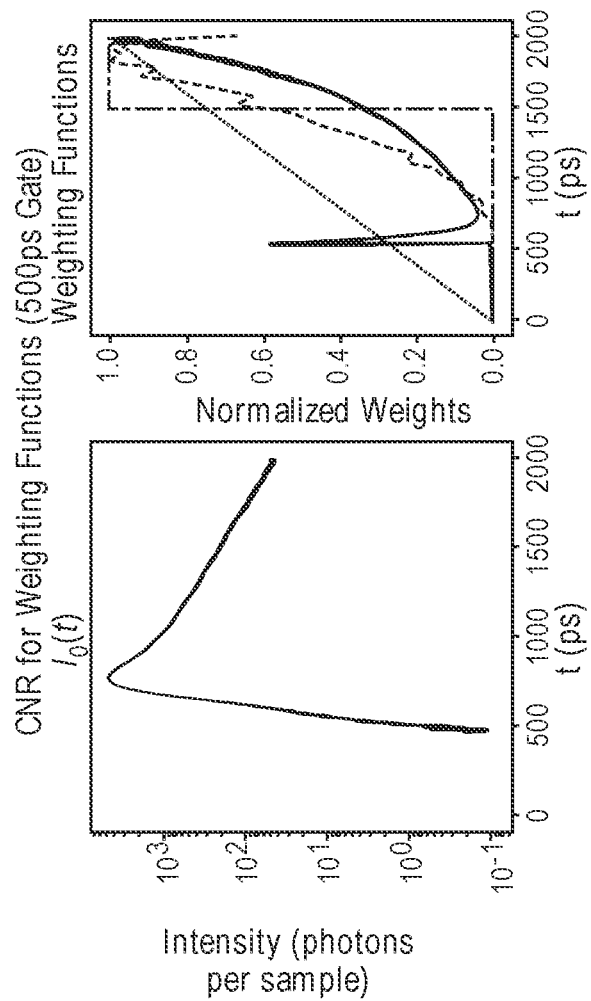
FIG. 11A
FIG. 11B

TIME-OF-FLIGHT OPTICAL MEASUREMENT AND DECODING OF FAST-OPTICAL SIGNALS

RELATED APPLICATION DATA

The present application is a continuation of U.S. patent application Ser. No. 16/533,133, filed Aug. 6, 2019, which claims the benefit of U.S. Provisional Patent Application Ser. No. 62/722,152, filed Aug. 23, 2018, which are expressly incorporated herein by reference.

FIELD OF THE INVENTION

The present inventions relate to methods and systems for non-invasive measurements in the human body, and in particular, methods and systems related to detecting physiological activity in the human body, animal body, and/or biological tissue.

BACKGROUND OF THE INVENTION

Measuring neural activity in the brain is useful for medical diagnostics, neuromodulation therapies, neuro engineering, or brain-computer interfacing. Conventional methods for measuring neural activity in the brain include diffusive optical imaging techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful radiation. Moreover, in contrast to other methods, such as functional magnetic resonance imaging (fMRI), these optically-based imaging methods do not require large magnets or magnetic shielding, and thus, can be scaled to wearable or portable form factors, which is especially important in applications, such as brain-computer interfacing.

There is an increasing interest in measuring fast-optical signals, which refers to changes in optical properties that occur when light propagating through active neural tissue (e.g., active brain tissue) is perturbed through a variety of mechanisms, including, but not limited to, cell swelling, cell volume change, changes in membrane potential, changes in membrane geometry, ion redistribution, birefringence changes, etc. (see Hill D. K. and Keynes, R. D., "Opacity Changes in Stimulated Nerve," J. Physiol., Vol. 108, pp. 278-281 (1949); Foust A. J. and Rector D. M., "Optically Teasing Apart Neural Swelling and Depolarization," Neuroscience, Vol. 145, pp. 887-899 (2007)). Because fast-optical signals are associated with neural activity, rather than hemodynamic responses, fast-optical signals may be used to detect brain activity with relatively high temporal resolution.

However, because optical measurement techniques rely on light, which scatters many times inside brain, skull, dura, pia, and skin tissues, the light paths occurring in these techniques comprise random or "diffusive" walks, and therefore, only limited sensitivity of fast-optical signals can be obtained by a conventional optical detector. The reason for this limited detection sensitivity of fast-optical signals is that the paths of photons striking the detector in such schemes are highly variable and difficult, and even impossible, to predict without detailed microscopic knowledge of the scattering characteristics of the brain volume of interest, which is typically unavailable in practice (i.e., in the setting of non-invasive measurements through skull for brain imaging and brain interfacing). In summary, light scattering has presented challenges for optical measurement techniques in achieving high sensitivity with regard to detecting fast-optical signals. Moreover, the diffusive nature of light propagation also creates challenges for measurements of fast changes in optical scattering inside tissue, since essentially all photons traveling between source and detector are highly diffused to begin with.

Nearly all diffusive optical measurement techniques to date offer relatively poor temporal resolution (100 ms-1 sec per sample), as they are primarily designed to detect hemodynamics that vary on a similarly slow time scale. Furthermore, some diffusive optical measurement techniques require relatively complicated circuitry for detecting a minute signal within the background light exiting the head. Known diffusive optical measurement techniques, although potentially capable of detecting the occurrence of a fast-optical signal, are not capable of effectively, reliably, and accurately measuring the intensity of a fast-optical signal (see Syre F, et al., "*Are VEP Corelated Fast Optical Signals Detectable in the Human Adult by Non-Invasive Nearinfrared Spectroscopy (NIRS)?*", Advances in Experimental Medicine and Biology. Vol. 530, pp. 421-431 (2003).

One type of diffusive optical measurement technique, referred to as frequency domain near infrared spectroscopy (FD-NIRS), measures fast-optical signals associated with neural activity by intensity modulating the light source at a specific modulation frequency (approximately 100 MHz) to sample the brain tissue (see Gratton G., Fabiani M, "*Fast-Optical Imaging of Human Brain Function*," Frontiers in Human Neuroscience, Vol. 4, Article 52, pp. 1-9 (June 2010)). However, because FD-NIRS modulates the light source at a frequency that is slower than the timescale of certain temporal features in fast-optical signals, i.e., slower than the timescales of time of flight variations in light propagation through the skin, skull and brain are that have been induced by fast-optical signals, FD-NIRS cannot efficiently or reliably detect these features, thereby limiting its detection sensitivity to fast-optical signals.

Furthermore, because FD-NIRS uses an AC modulated, but continuous light source, it is always receiving a mixture of the signal photons from the brain and shallow photons that never reach the brain. There are several orders of magnitude more of these shallow photons than signal photons, giving FD-NIRS an enormous background that adds shot noise, increases necessary dynamic range on the photon detector, etc. Some of these unwanted shallow photons can be eliminated by separating the source and detector a relatively long distance from each other (e.g., in the range of several centimeters). However, this solution results in a significant loss of detected photons and significantly decreases the spatial resolution of the measurement.

Another type of diffusive optical imaging technique, referred to as interferometric Near-Infrared Spectroscopy (iNIRS) (see Borycki, Dawid, Kholiqov, Oybek, Chong, Shau Poh, Srinivasan, Vivek J., "*Interferometric Near-Infrared Spectroscopy (iNIRS) for Determination of Optical and Dynamical Properties of Turbid Media*," Optics Express, Vol. 24, No. 1, Jan. 11, 2016), as well as swept source optical coherence tomography (SS-OCT), utilizes holographic methods to resolve the times of flight of light traveling through the skin, skull and brain, and thus reports on information that could be indicative of fast optical signals. In particular, these holographic methods mix the detected light, which takes the form of a spatially disordered speckle interference pattern, against a reference beam, thereby requiring a relatively complicated and expensive arrangement of components. Further, while the iNIRS or SS-OCT approaches are very sophisticated, they require the detection and measurement of speckles, presenting challenges in a highly attenuating medium, such as the human body, due to the very low number of photons that reach each detector. Thus, a camera with very large number of detectors (or pixels) are required to sufficiently detect many dim speckles, thereby further increasing the complexity and expense of the system. This complexity and expense will, of course, be magnified as the iNIRS system or SS-OCT system is scaled to increase the number of optical source-detector pairs for x-y (non-depth) spatial resolution. Furthermore, even the fastest cameras, required to detect the speckles, are much slower than a single detector, and thus, the detection speed of the speckle interference pattern is limited in the iNIRS approach. The iNIRS approach has also not yet been demonstrated to detect fast-optical signals.

Another type of diffusive optical imaging technique is a time resolved DOT approach that uses a single-photon avalanche diode (SPAD) to collect photons one at a time (see Mu, Ying and Niedre, Mark, "*Fast Single Photon Avalanche Photodiode-Based Time-Resolved Diffuse Optical Tomography Scanner*," Optical Express, Vol. 6, No. 9, Aug. 26, 2015). However, this approach requires a complicated electronic circuit and is limited on the number of photons that can be counted as a unit of time. Furthermore, this DOT approach has not yet been demonstrated to detect fast-optical signals.

There, thus, remains a need to provide a relatively simple optical measurement system for measuring the intensity of biologically intrinsic signals, such as fast-optical signals, in the brain at a sufficient temporal resolution and sensitivity.

SUMMARY OF THE INVENTION

In accordance with a first aspect of the present inventions, an optical measurement system comprises an optical source configured for delivering sample light in an anatomical structure (e.g., a brain), such that the sample light is scattered and absorbed by the anatomical structure, resulting in physiological-encoded signal light that exits the anatomical structure. The optical measurement further comprises an optical detector configured for detecting the physiological-encoded signal light. In one embodiment, the sample light comprises a single pulse, e.g., having an optical pulse width of less than 1 ns, and perhaps even less than 100 ps. In this case, the optical detector may comprise a photodiode (e.g., a metal-semiconductor-metal (MSM) photodiode and a PIN diode) configured for detecting the physiological-encoded signal light.

The optical measurement system further comprises a processor configured for acquiring an initial time-of-flight (TOF) profile derived from the physiological-encoded signal light. The initial TOF profile has an initial contrast-to-noise ratio (CNR) between a plurality states (e.g., an active state and an inactive state, or at least two different active states) of a physiological activity (e.g., a fast-optical signal) in the anatomical structure.

The processor is further configured for applying one or more weighting functions to the initial TOF profile to generate a weighted TOF profile having a subsequent CNR greater than the initial CNR between the plurality of states of the physiological activity. In one embodiment, the weighting function(s) comprises a fractional power, such as ½, and/or a ramp function. In another embodiment, the weighting function may be a change in intensity between a plurality of reference TOF profiles respectively corresponding to the plurality of states of the physiological activity. The processor is further configured for processing the weighted TOF profile, and identifying one of the plurality of states of the physiological activity based on the processed TOF profile.

In one embodiment, the processor is configured for processing the weighted TOF profile by reducing the weighted TOF profile to a single index value indicative of the one state of the physiological activity (e.g., by computing an area of the weighted TOF profile), in which case, the processor may be configured for identifying the one state of the physiological activity based on the single index value. The optical detector may be configured for deriving the initial TOF profile from the physiological-encoded signal light by directly detecting the initial TOF profile of the physiological-encoded signal light, in which case, at least a portion of the processor may comprise an analog circuit configured for applying the weighting function(s) to the initial TOF profile to generate the weighted TOF profile, and reducing the weighted TOF profile to the single index value, and a digitizer configured for digitizing the single index value, and another portion of the processor is configured for identifying the one state of the physiological activity based on the single digitized index value. In another embodiment, the optical detector is configured for detecting a frequency domain representation of the physiological-encoded signal light, wherein the processor is configured for deriving the initial TOF profile from the physiological-encoded signal light by transforming the frequency domain representation of the physiological-encoded signal light into the initial TOF profile.

In accordance with a second aspect of the present inventions, an optical measurement method comprises delivering sample light in an anatomical structure (e.g., a brain), such that the sample light is scattered by the anatomical structure, resulting in physiological-encoded signal light that exits the anatomical structure. The optical measurement method further comprises detecting the physiological-encoded signal light. In one method, the sample light comprises a single pulse, e.g., having an optical pulse width of less than 1 ns, and perhaps even less than 100 ps. In this case, the physiological-encoded signal light may be detected by a photodiode (e.g., a metal-semiconductor-metal (MSM) photodiode and a PIN diode).

The optical measurement method further comprises acquiring an initial time-of-flight (TOF) profile derived from the detected physiological-encoded signal light. The initial TOF profile has an initial contrast-to-noise ratio (CNR) between a plurality states (e.g., an active state and an inactive state, or at least two different active states) of a physiological activity (e.g., a fast-optical signal) in the anatomical structure.

The method further comprises applying one or more weighting functions to the initial TOF profile to generate a weighted TOF profile having a subsequent CNR greater than the initial CNR between the plurality of states of the physiological activity. In one method, the weighting function(s) comprises a fractional power, such as ½, and/or a ramp function. In another method, the weighting function may be a change in intensity between a plurality of reference TOF profiles respectively corresponding to the plurality of states of the physiological activity. The method further comprises processing the weighted TOF profile, and identifying one of the plurality of states of the physiological activity based on the processed TOF profile.

In one method, the weighted TOF profile is processed by reducing the weighted TOF profile to a single index value indicative of the one state of the physiological activity (e.g., by computing an area of the weighted TOF profile), in which case, the one state of the physiological activity is identified based on the single index value. The initial TOF profile may be derived from the physiological-encoded signal light by directly detecting the initial TOF profile of the physiological-encoded signal light, in which case, the weighting function(s) may be applied to the initial TOF profile to generate the weighted TOF profile, the weighted TOF profile may be reduced to the single index value in an analog manner, the optical measurement method may further comprise digitizing the single index value, and the one state of the physiological activity may be identified based on the single digitized index value. Another method comprises detecting a frequency domain representation of the physiological-encoded signal light, in which case, the initial TOF profile may be derived from the physiological-encoded signal light by transforming the frequency domain representation of the physiological-encoded signal light into the initial TOF profile.

In accordance with a third aspect of the present inventions, an optical measurement system comprises an optical source configured for delivering sample light in an anatomical structure (e.g., a brain), such that the sample light is scattered and absorbed by the anatomical structure, resulting in physiological-encoded signal light that exits the anatomical structure. The optical measurement further comprises an optical detector configured for detecting the physiological-encoded signal light. In one embodiment, the sample light comprises a single pulse, e.g., having an optical pulse width of less than 1 ns, and perhaps even less than 100 ps. In this case, the optical detector may comprise a photodiode (e.g., a metal-semiconductor-metal (MSM) photodiode and a PIN diode) configured for detecting the physiological-encoded signal light.

The optical measurement system further comprises a processor configured for acquiring an initial time-of-flight (TOF) profile derived from the physiological-encoded signal light, and applying a weighting function to the initial TOF profile to generate a weighted TOF profile that has a decreased variance in the shot noise. In one embodiment, the weighting function(s) comprises a fractional power, such as ½, and/or a ramp function. In another embodiment, the weighting function may be a change in intensity between a plurality of reference TOF profiles respectively corresponding to the plurality of states of the physiological activity.

The processor is further configured for processing the weighted TOF profile, and identifying one of a plurality of states (e.g., an active state and an inactive state, or at least two different active states) of a physiological activity (e.g., a fast-optical signal) in the anatomical structure based on the processed TOF profile.

In one embodiment, the processor is configured for processing the weighted TOF profile by reducing the weighted TOF profile to a single index value indicative of the one state of the physiological activity, in which case, the processor may be configured for identifying the one state of the physiological activity based on the single index value. As one example, the processor may be configured for reducing the weighted TOF profile to the single index value by computing a centroid of the weighted TOF profile. As another example, the processor may be configured for reducing the weighted TOF profile to the single index value by computing a dot product of the TOF profile and a reference active TOF profile to yield an active state correlation coefficient $C_a$, computing a dot product of the weighted TOF profile and a reference inactive TOF profile to yield an inactive state correlation coefficient $C_i$, and computing the single index value $\alpha$ in accordance with the equation $$\alpha = \frac{C_a - C_i}{C_a + C_i}.$$

As still another example, the processor may be configured for reducing the TOF profile to the single index value by computing a dot product of the weighted TOF profile and a singular value decomposition of a first reference active TOF profile to yield a first active state correlation coefficient $C_1$, computing a dot product of the weighted TOF profile and a singular value decomposition of a second reference active TOF profile to yield a second active state correlation coefficient $C_2$, and computing the single index value $\alpha$ in accordance with the equation $$\alpha = \frac{C_1 - C_2}{C_1 + C_2}.$$

The optical detector may be configured for deriving the initial TOF profile from the physiological-encoded signal light by directly detecting the initial TOF profile of the physiological-encoded signal light, in which case, at least a portion of the processor may comprise an analog circuit configured for applying the weighting function(s) to the initial TOF profile to generate the weighted TOF profile, and reducing the weighted TOF profile to the single index value, and a digitizer configured for digitizing the single index value, and another portion of the processor is configured for identifying the one state of the physiological activity based on the single digitized index value. In another embodiment, the optical detector is configured for detecting a frequency domain representation of the physiological-encoded signal light, wherein the processor is configured for deriving the initial TOF profile from the physiological-encoded signal light by transforming the frequency domain representation of the physiological-encoded signal light into the initial TOF profile.

In accordance with a fourth aspect of the present inventions, an optical measurement method comprises delivering sample light in an anatomical structure (e.g., a brain), such that the sample light is scattered by the anatomical structure, resulting in physiological-encoded signal light that exits the anatomical structure. The optical measurement method further comprises detecting the physiological-encoded signal light. In one method, the sample light comprises a single pulse, e.g., having an optical pulse width of less than 1 ns, and perhaps even less than 100 ps. In this case, the physiological-encoded signal light may be detected by a photodiode (e.g., a metal-semiconductor-metal (MSM) photodiode and a PIN diode).

The optical measurement method further comprises acquiring an initial time-of-flight (TOF) profile derived from the physiological-encoded signal light, and applying a weighting function to the initial TOF profile to generate a weighted TOF profile that has a decreased variance in the shot noise. In one method, the weighting function(s) comprises a fractional power, such as ½, and/or a ramp function. In another method, the weighting function may be a change in intensity between a plurality of reference TOF profiles respectively corresponding to the plurality of states of the physiological activity. The method further comprises processing the weighted TOF profile, and identifying one of a plurality of states (e.g., an active state and an inactive state, or at least two different active states) of the physiological activity (e.g., a fast-optical signal) based on the processed TOF profile.

In one method, the weighted TOF profile is processed by reducing the weighted TOF profile to a single index value indicative of the one state of the physiological activity (e.g., by computing an area of the weighted TOF profile), in which case, the one state of the physiological activity is identified based on the single index value. As one example, the weighted TOF profile may be reduced to the single index value by computing a centroid of the weighted TOF profile. As another example, the weighted TOF profile may be reduced to the single index value by computing a dot product of the TOF profile and a reference active TOF profile to yield an active state correlation coefficient $C_a$, computing a dot product of the weighted TOF profile and a reference inactive TOF profile to yield an inactive state correlation coefficient $C_i$, and computing the single index value α in accordance with the equation $$\alpha = \frac{C_a - C_i}{C_a + C_i}.$$

As still another example, the TOF profile may be reduced to the single index value by computing a dot product of the weighted TOF profile and a singular value decomposition of a first reference active TOF profile to yield a first active state correlation coefficient $C_1$, computing a dot product of the weighted TOF profile and a singular value decomposition of a second reference active TOF profile to yield a second active state correlation coefficient $C_2$, and computing the single index value α in accordance with the equation $$\alpha = \frac{C_1 - C_2}{C_1 + C_2}.$$

The initial TOF profile may be derived from the physiological-encoded signal light by directly detecting the initial TOF profile of the physiological-encoded signal light, in which case, the weighting function(s) may be applied to the initial TOF profile to generate the weighted TOF profile, the weighted TOF profile may be reduced to the single index value in an analog manner, the optical measurement method may further comprise digitizing the single index value, and the one state of the physiological activity may be identified based on the single digitized index value. Another method comprises detecting a frequency domain representation of the physiological-encoded signal light, in which case, the initial TOF profile may be derived from the physiological-encoded signal light by transforming the frequency domain representation of the physiological-encoded signal light into the initial TOF profile.

In accordance with a fifth aspect of the present inventions, an optical measurement system comprises an optical source configured for delivering sample light in an anatomical structure (e.g., a brain), such that the sample light is scattered and absorbed by the anatomical structure, resulting in physiological-encoded signal light that exits the anatomical structure. The optical measurement further comprises an optical detector configured for detecting the physiological-encoded signal light. In one embodiment, the sample light comprises a single pulse, e.g., having an optical pulse width of less than 1 ns, and perhaps even less than 100 ps. In this case, the optical detector may comprise a photodiode (e.g., a metal-semiconductor-metal (MSM) photodiode and a PIN diode) configured for detecting the physiological-encoded signal light.

The optical measurement system further comprises a processor configured for acquiring an initial time-of-flight (TOF) profile derived from the physiological-encoded signal light, for applying a fractional power (e.g., ½) to the initial TOF profile to generate a pre-conditioned TOF profile, for computing the centroid of the pre-conditioned TOF profile to generate a single index value indicative of one of a plurality of states (e.g., an active state and an inactive state, or at least two different active states) of a physiological activity (e.g., a fast-optical signal) in the anatomical structure, and identifying the one state of the physiological activity based on the single index value.

In one embodiment, the optical detector may be configured for deriving the initial TOF profile from the physiological-encoded signal light by directly detecting the initial TOF profile of the physiological-encoded signal light, in which case, at least a portion of the processor comprises an analog circuit configured for applying the fractional power to the initial TOF profile to generate the pre-conditioned TOF profile, and computing the centroid of the pre-conditioned TOF profile to generate the single index value, and a digitizer configured for digitizing the single index value, and another portion of the processor is configured for identifying the one state of the physiological activity based on the single digitized index value. In another embodiment, the optical detector is configured for detecting a frequency domain representation of the physiological-encoded signal light, wherein the processor is configured for deriving the initial TOF profile from the physiological-encoded signal light by transforming the frequency domain representation of the physiological-encoded signal light into the initial TOF profile.

In accordance with a sixth aspect of the present inventions, an optical measurement method comprises delivering sample light in an anatomical structure (e.g., a brain), such that the sample light is scattered by the anatomical structure, resulting in physiological-encoded signal light that exits the anatomical structure. The optical measurement method further comprises detecting the physiological-encoded signal light. In one method, the sample light comprises a single pulse, e.g., having an optical pulse width of less than 1 ns, and perhaps even less than 100 ps. In this case, the physiological-encoded signal light may be detected by a photodiode (e.g., a metal-semiconductor-metal (MSM) photodiode and a PIN diode).

The optical measurement method further comprises acquiring an initial time-of-flight (TOF) profile derived from the detected physiological-encoded signal light, and applying a fractional power (e.g., ½) to the initial TOF profile to generate a pre conditioned TOF profile, computing the centroid of the pre-conditioned TOF profile to generate a single index value indicative of one of a plurality of states (e.g., an active state and an inactive state, or at least two different active states) of a physiological activity (e.g., a fast-optical signal) in the anatomical structure, and identifying the one state of the physiological activity based on the single index value.

In one method, the initial TOF profile is derived from the physiological-encoded signal light by directly detecting the initial TOF profile of the physiological-encoded signal light, in which case, the fractional power may be applied to the initial TOF profile in analog manner to generate the pre-conditioned TOF profile, the centroid of the pre-conditioned TOF profile may be computed in an analog manner to generate the single index value, the optical measurement method may further comprise digitizing the single index value, and the one state of the physiological activity may be identified based on the single digitized index value. Another method comprises detecting a frequency domain representation of the physiological-encoded signal light, in which case, the initial TOF profile may be derived from the physiological-encoded signal light by transforming the frequency domain representation of the physiological-encoded signal light into the initial TOF profile.

In accordance with a seventh aspect of the present inventions, an optical measurement system comprises an optical source configured for delivering sample light in an anatomical structure (e.g., a brain), such that the sample light is scattered and absorbed by the anatomical structure, resulting in physiological-encoded signal light that exits the anatomical structure. The optical measurement further comprises an optical detector configured for detecting the physiological-encoded signal light. In one embodiment, the sample light comprises a single pulse, e.g., having an optical pulse width of less than 1 ns, and perhaps even less than 100 ps. In this case, the optical detector may comprise a photodiode (e.g., a metal-semiconductor-metal (MSM) photodiode and a PIN diode) configured for detecting the physiological-encoded signal light.

The optical measurement system further comprises an analog circuit configured for reducing the TOF profile to a single index value indicative of one of a plurality of states (e.g., an active state and an inactive state, or at least two different active states) of a physiological activity (e.g., a fast-optical signal) in the anatomical structure, and identifying the one state of the physiological activity based on the single index value. The optical measurement system further comprises a processor configured for identifying the one state of the physiological activity based on the single index value.

In one embodiment, the optical measurement system further comprises a digitizer configured for digitizing the single index value, in which case, the processor may be configured for identifying the one state of the physiological activity based on the single digitized index value. In another embodiment, the analog circuit may be configured for reducing the TOF profile to the single index value by computing a centroid of the TOF profile, e.g., by computing an area of the TOF profile. The still another embodiment, the analog circuit may be configured for applying a fractional power (e.g., ½) to the TOF profile to generate a pre-conditioned TOF profile, and reducing the TOF profile to the single index value by computing a centroid of the pre-conditioned TOF profile.

In accordance with an eighth aspect of the present inventions, an optical measurement method comprises delivering sample light in an anatomical structure (e.g., a brain), such that the sample light is scattered by the anatomical structure, resulting in physiological-encoded signal light that exits the anatomical structure. The optical measurement method further comprises detecting the physiological-encoded signal light. In one method, the sample light comprises a single pulse, e.g., having an optical pulse width of less than 1 ns, and perhaps even less than 100 ps. In this case, the physiological-encoded signal light may be detected by a photodiode (e.g., a metal-semiconductor-metal (MSM) photodiode and a PIN diode).

The optional measurement system further comprises directly detecting a time-of-flight (TOF) profile of the physiological-encoded signal light, and reducing the TOF profile to a single index value in an analog manner. The single index value is indicative of one of a plurality of states (e.g., an active state and an inactive state, or at least two different active states) of a physiological activity (e.g., a fast-optical signal) in the anatomical structure. The method further comprises identifying the one state of the physiological activity based on the single index value.

One optical measurement method further comprises digitizing the single index value, wherein the one state of the physiological activity is identified based on the single digitized index value. In another method, the TOF profile is reduced to the single index value by computing a centroid of the TOF profile in an analog manner. Still another method further comprises applying a fractional power (e.g., ½) to the TOF profile in an analog manner to generate a pre-conditioned TOF profile, in which case, the TOF profile may be reduced to the single index value by computing a centroid of the pre-conditioned TOF profile in an analog manner.

In accordance with a ninth aspect of the present inventions, an optical measurement system comprises an optical source configured for delivering sample light in the form of a single pulse (e.g., having an optical pulse width of less than 1 ns, and perhaps even less than 100 ps) in an anatomical structure (e.g., a brain), such that the sample light is scattered and absorbed by the anatomical structure, resulting in physiological-encoded signal light in the form of an intensity impulse response that exits the anatomical structure. The optical measurement further comprises an optical detector (e.g., a photodiode, such as a metal-semiconductor-metal (MSM) photodiode and a PIN diode) configured for directly detecting the intensity impulse response representing a time-of-flight (TOF) profile of the physiological-encoded signal light. The optical measurement system further comprises a processor configured for identifying one of a plurality of states (e.g., an active state and an inactive state, or at least two different active states) of a physiological activity (e.g., a fast-optical signal) in the anatomical structure.

In one embodiment, the optical measurement system further comprises an analog circuit configured for reducing the TOF profile to a single index value indicative of the one state of the physiological activity in the anatomical structure, in which case, processor may be configured for identifying the one state of the physiological activity based on the single index value. The optical measurement system may further comprise digitizer configured for digitizing the single index value, in which case, the processor may be configured for identifying the one state of the physiological activity based on the single digitized index value. The analog circuit may be configured for reducing the TOF profile to the single index value by computing a centroid of the TOF profile, computing an area of the TOF profile. The analog circuit may be further configured for applying a fractional power (e.g., ½) to the TOF profile to generate a pre conditioned TOF profile, and reducing the TOF profile to the single index value by computing a centroid of the pre-conditioned TOF profile.

In accordance with a tenth aspect of the present inventions, an optical measurement method comprises delivering sample light in the form of a single pulse (e.g., having an optical pulse width of less than 1 ns, and perhaps even less than 100 ps) in an anatomical structure (e.g., a brain), such that the sample light is scattered by the anatomical structure, resulting in physiological-encoded signal light in the form of an intensity impulse response that exits the anatomical structure.

The optical measurement method further comprises directly detecting the intensity impulse response representing a time-of-flight (TOF) profile of the physiological-encoded signal light, e.g., using a photodiode, such as a metal-semiconductor-metal (MSM) photodiode and a PIN diode. The optical measurement method further comprises identifying one of a plurality of states (e.g., an active state and an inactive state, or at least two different active states) of a physiological activity (e.g., a fast-optical signal) in the anatomical structure.

One optical measurement method further comprises reducing the TOF profile to a single index value in an analog manner. The single index value is indicative of the one states of the physiological activity in the anatomical structure, in which case, the one state of the physiological activity may be identified based on the single index value. The optical measurement method may further comprise digitizing the single index value, in which case, the one state of the physiological activity may be identified based on the single digitized index value. The TOF profile may be reduced to the single index value by computing a centroid of the TOF profile in an analog manner. The optical measurement method may further comprise applying a fractional power (e.g., ½) to the TOF profile in an analog manner to generate a pre-conditioned TOF profile, in which case, the TOF profile may be reduced to the single index value by computing a centroid of the pre-conditioned TOF profile in an analog manner.

In accordance with an eleventh aspect of the present inventions, an optical measurement system comprises an optical source configured for delivering sample light in an anatomical structure (e.g., a brain), such that the sample light is scattered and absorbed by the anatomical structure, resulting in physiological-encoded signal light that exits the anatomical structure. The optical measurement further comprises an optical detector configured for detecting the physiological-encoded signal light.

The optical measurement system further comprises a processor configured for acquiring a time-of-flight (TOF) profile derived from the physiological-encoded signal light, reducing the TOF profile to a single index value indicative of one of a plurality of states (e.g., an active state and an inactive state, or at least two different active states) of a physiological activity in the anatomical structure, and identifying the one state of the physiological activity (e.g., a fast-optical signal) based on the single index value.

In one embodiment, the processor may be configured for reducing the TOF profile to the single index value by computing a centroid of the TOF profile. In another embodiment, the processor may be configured for reducing the TOF profile to the single index value by computing a dot product of the TOF profile and a reference active TOF profile to yield an active state correlation coefficient $C_a$, computing a dot product of the TOF profile and a reference inactive TOF profile to yield an inactive state correlation coefficient $C_i$, and computing the single index value $\alpha$ in accordance with the equation $$\alpha = \frac{C_a - C_i}{C_a + C_i}.$$

In still another embodiment, the processor may be configured for reducing the TOF profile to the single index value by computing a dot product of the TOF profile and a singular value decomposition of a first reference active TOF profile to yield a first active state correlation coefficient $C_1$, computing a dot product of the TOF profile and a singular value decomposition of a second reference active TOF profile to yield a second active state correlation coefficient $C_2$, and computing the single index value $\alpha$ in accordance with the equation $$\alpha = \frac{C_1 - C_2}{C_1 + C_2}.$$

In accordance with a twelfth aspect of the present inventions, an optical measurement method comprises delivering sample light in an anatomical structure (e.g., a brain), such that the sample light is scattered by the anatomical structure, resulting in physiological-encoded signal light that exits the anatomical structure. The optical measurement method further comprises detecting the physiological-encoded signal light.

The optional measurement method further comprises acquiring a time-of-flight (TOF) profile derived from the physiological-encoded signal light, reducing the TOF profile to a single index value indicative of one of a plurality of states (e.g., an active state and an inactive state, or at least two different active states) of a physiological activity (e.g., a fast-optical signal) in the anatomical structure, and identifying the one state of the physiological activity based on the single index value.

In one method, the TOF profile is processed by reducing the weighted TOF profile to a single index value indicative of the one state of the physiological activity (e.g., by computing an area of the weighted TOF profile), in which case, the one state of the physiological activity is identified based on the single index value. As one example, the TOF profile may be reduced to the single index value by computing a centroid of the TOF profile. As another example, the TOF profile may be reduced to the single index value by computing a dot product of the TOF profile and a reference active TOF profile to yield an active state correlation coefficient $C_a$, computing a dot product of the weighted TOF profile and a reference inactive TOF profile to yield an inactive state correlation coefficient $C_i$, and computing the single index value $\alpha$ in accordance with the equation $$\alpha = \frac{C_a - C_i}{C_a + C_i}.$$

As still another example, the TOF profile may be reduced to the single index value by computing a dot product of the TOF profile and a singular value decomposition of a first reference active TOF profile to yield a first active state correlation coefficient $C_1$, computing a dot product of the TOF profile and a singular value decomposition of a second reference active TOF profile to yield a second active state correlation coefficient $C_2$, and computing the single index value $\alpha$ in accordance with the equation $$\alpha = \frac{C_1 - C_2}{C_1 + C_2}.$$

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 5A is an experimental optical detection system;

FIG. 11A is a diagram illustrating a comparison of simulated weighting functions applied by the optical measurement system of FIG. 1 and a prior art system to an experimental TOF profile to increase the contrast to noise ratio (CNR) by applying a weighting function to a TOF profile, assuming no gate in the detection of the TOF profile;

FIG. 11B is a diagram illustrating a comparison of simulated weighting functions applied by the optical measurement system of FIG. 1 and a prior art system to an experimental TOF profile to increase the contrast to noise ratio (CNR) by applying a weighting function to a TOF profile, assuming a 500 ps gate in the detection of the TOF profile;

DETAILED DESCRIPTION OF THE EMBODIMENTS

Figure 1:
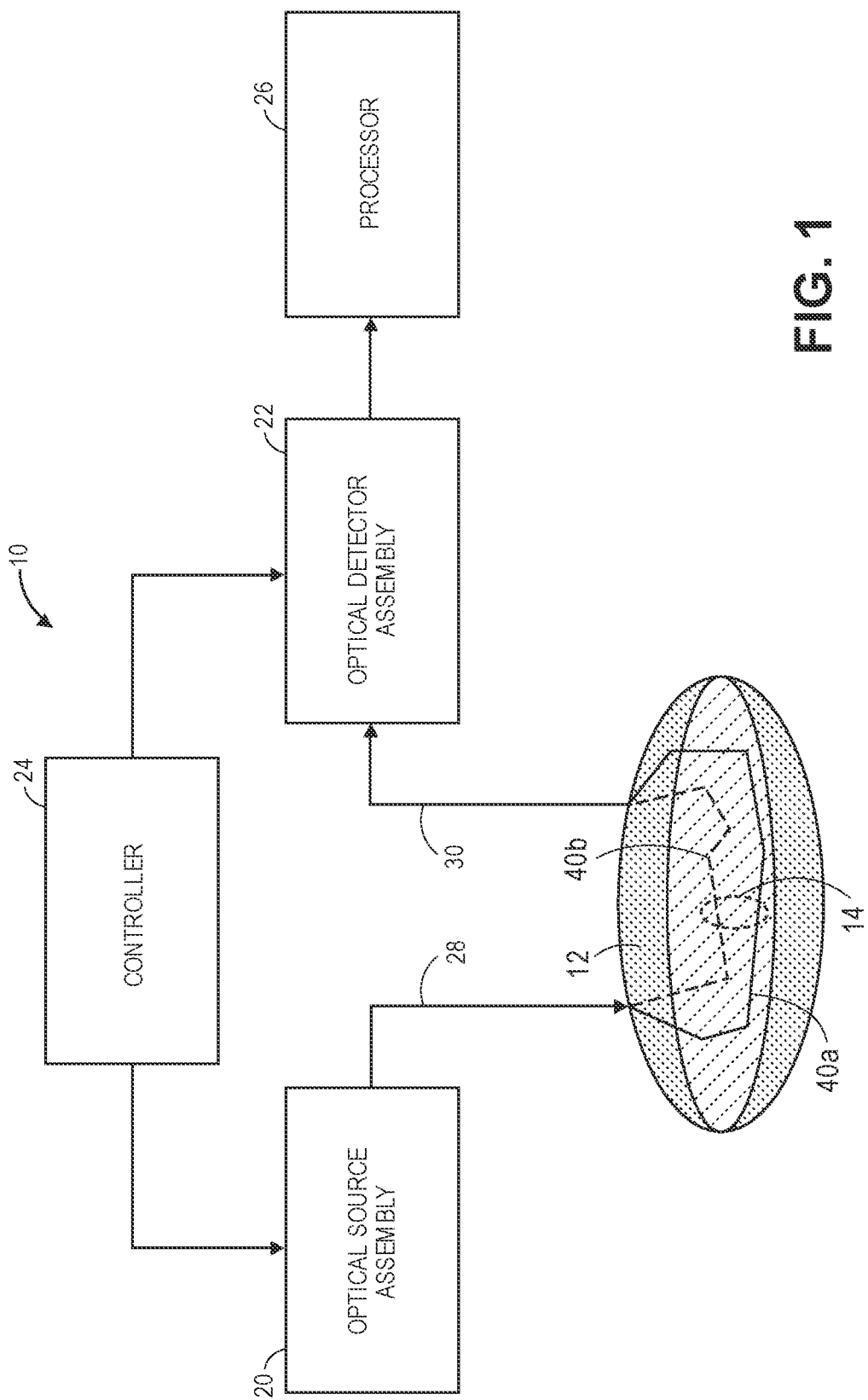
FIG. 1 is a block diagram of an optical measurement system constructed in accordance with one embodiment of the present inventions.

Referring to FIG. 1, one embodiment of an optical measurement 10 (and variations thereof) constructed in accordance with the present inventions will be described. The optical measurement system 10 is designed to non-invasively acquire physiological-encoded signal light (i.e., signal light representative of a physiologically-dependent optical parameter) in an anatomical structure 12 via one or more optical paths 14, processing the physiological-encoded signal light, and distinguishing between states of a physiological activity within the anatomical structure 12.

It should be appreciated that the term "state," in the absolute sense, is arbitrary, and is only meaningful in the relative sense when compared to other states. For example, the physiological activity may have either an active state or an inactive state in a binary sense (either the physiological activity is present or the physiological activity is absent), or the physiological activity may have many (even an infinite amount of) states along a discrete range or a continuum. Thus, in distinguishing between states of the physiological activity, the optical measurement system 10 can either measure the physiological activity in a binary fashion (the physiological activity may be either present or absent), in which case, the optical measurement system 10 may determine whether or not the physiological activity is present, or measure the degree of activity of a physiological activity in a discrete or continuous range, in which case, the optical measurement systems 10 may determine discrete or continuous intensities of the physiological activity. Thus, the novel techniques described herein allow the optical measurement system 10 to distinguish between arbitrary states of a physiological activity, regardless of whether the optical measurement system 10 measures the physiological activity in a binary, discrete, or continuous sense.

In distinguishing between states of the physiological activity in the anatomical structure 12, one advantageous embodiment of the optical measurement system 10 directly analyzes a time-of-flight (TOF) profile of physiological-encoded signal light that exits the anatomical structure 12 in response to the delivery of sample light into the anatomical structure 12. Such embodiment of the optical measurement system 10 may further advantageously utilize direct analog and rapidly-sampled high-bandwidth detection (e.g., in the several GHz range) of a full "intensity impulse response" of the signal light that yields the TOF profile to reveal through analog signal processing, prior to digitization, fast-optical signals encoded in the form of precise shape changes in the TOF profile that are otherwise hidden from prior art optical detection techniques. This allows the form factor, energy consumption, and cost of the optical measurement system 10 to be decreased enough to allow commercialization of a wearable device for, e.g., neural measurements. Furthermore, by selecting the response of the optical measurement system 10 to reject continuous background light (high pass filtering above 10 MHz), it is possible to perform measurements in a non-contact manner. In other words, such wearable device need not be in contact with skin in order to block out all of the environmental light. Furthermore, by delivering the sample light as a fast pulse, all of the signal below 10 MHz can easily be rejected without any degradation in contrast.

Such advantageous embodiment of the optical measurement system 10 is capable of generating sample light with relatively short pulse widths to produce signal light having a high frequency bandwidth, and directly extracting the TOF profile from the signal light (i.e., without having to use a Fast Fourier Transform (FFT) to transform the detected signal light from a frequency domain representation to a time domain representation that would otherwise require heavy power consumption and additional digital circuitry). The direct measurement of the TOF profile from the signal light also allows the shape of the TOF profile to be analyzed at a high resolution.

Regardless of whether the TOF profile is acquired in the advantageous analog manner described above, or alternatively in a digital manner, the optical measurement system 10 utilizes one or more novel techniques to analyze a TOF profile in a more noise-robust and photon-efficient manner to reveal the occurrence, as well as the intensity, of a physiological activity in the anatomical structure in a minimal amount of time. These novel techniques may outperform existing fast-optical signal measurement approaches, such as conventional FD-NIRS, by orders of magnitude in sensitivity at a fixed photon budget, and may even approach a mathematical optimum in terms of discriminating between states of a physiological activity.

One advantageous embodiment of the optical measurement system 10 accomplishes this by pre-conditioning the TOF profile to increase the contrast-to-noise ratio (CNR) between states of a physiological activity (different amounts of optical scattering, including no optical scattering) within tissue, thereby maximizing the sensitivity in distinguishing the states of the physiological activity in a remarkable and unexpected manner. Such advantageous embodiment of the optical measurement system 10 may pre-condition the TOF profile by applying a weighting function that reduces the variance in shot noise over the TOF profile, which has been discovered to greatly increase the sensitivity in distinguishing states of physiological activity.

Another advantageous embodiment of the optical measurement system 10 leverages the direct analog and high-bandwidth detection of the TOF profile described above to process such TOF profiles in an analog manner prior to digitization, and in particular, by reducing the TOF profile to a single index value indicative a state of the physiological activity, such that only one value needs to be digitized. This leads to optimization of data capture and processing that reduces the time, amount of processing, power consumption, and other metrics, e.g., for efficient on-chip processing in the context of wearable devices. This "all-analog processing" enables relaxed data throughput and power requirements and a more miniaturized form factor, as well as faster processing, by creating representations of the TOF profile that is more suitable for downstream analysis, which is robust to noise. This further enables scaling to larger channel counts (i.e., multiple optical-source pairs) in a wearable form factor.

Another advantage of the optical measurement 10 is that it does not require holography, and as such, does not require the additional components required by holography, and furthermore, can utilize detectors, such as large photodiodes, that can be, for example, on the order of 10,000× or larger than a single speckle, and therefore collect many more photons, leading to higher signal to noise ratio. Furthermore, compared to even the fastest cameras, the detection speed of the TOF profile can be increased with the use of a single or small number of detectors.

In the illustrated embodiment, the anatomical structure 12 is a brain, in which case, the optical measurement system 10 (or a device external to the optical measurement system 10) may identify the occurrence, extent of, and location of neural activity within the brain 12 on the detected physiological activity. Although for exemplary purposes, the optical measurement system 10 is described herein as being used to acquire physiological-encoded data from brain tissue, variations of such optical measurement system 10 may be used to acquire physiological-encoded data from other anatomical structures of a human body, animal body, and/or biological tissue.

A further advantage of the optical measurement system 10 is that it allows separation of the early-arriving photons from the later arriving component. The vast majority of these photons do not reach the brain tissue (or other deep tissue target of interest, in other embodiments), and they are far more numerous than the photons that do reach brain tissue. These photons can be time-gated out of the signal, reducing the required dynamic range of the optical measurement system 10. The optical measurement system 10 can also be used for detection of ancillary signals, such as heartbeat pulsatile signals, or physiological changes in the skin itself. These signals provide useful data in their own right, but can also be used to help artifact and noise removal from TOF profile. Light that passes through the brain 12 will necessarily pass through the skin and have the skin changes and heartbeat changes overlaid on the brain signal. Separate recording of those signals via the early-arriving photons simplifies an extremely difficult challenge of detecting minute brain signals in the face of much larger artifacts. Only by having TOF profiles can this be done: in the prior art, all shallow photons are inextricably mixed with deeper photons, contributing no brain signal, but adding shot noise and increasing artifact amplitude.

In the illustrated embodiments, the physiological-encoded data acquired by the optical measurement system 10 is neural activity data, and the physiological activity is reflected in a fast-optical signal (i.e., perturbations in the TOF profile due to changes in the optical properties of neural tissue caused by mechanisms related to the depolarization of neural tissue, including, but not limited to, cell swelling, cell volume change, changes in membrane potential, changes in membrane geometry, ion redistribution, birefringence changes, macroscopic motion, change in mechanical stiffness of tissue, etc.), although in alternative embodiments, the physiological activity may be a slower hemodynamic change, e.g., Doppler shift due to moving blood flow, changes in blood volume, metabolism variations such a blood oxygen changes. However, as will be described in further detail below, the optical measurement system 10, when properly tuned to a specific type of physiological activity, is capable of decoding light propagating through the brain to detect any physiological activity that causes a change in an optical property of the brain 12.

The neural activity information (or the acquired neural-encoded data from which it is derived) may be transmitted to external programmable devices for use (e.g., computed, processed, stored, etc.) therein, e.g., medical devices, entertainment devices, neuromodulation stimulation devices, lie detection devices, alarm systems, educational games, brain interface devices, etc., and/or may be used internally to adjust the detection parameters of the optical measurement systems described herein, such as increasing or decreasing the strength of the optical source and/or data compression and/or analysis, such a Fast Fourier Transform (FFT) and/or statistical analysis.

Although the optical measurement system 10, for purposes of brevity, is described herein as acquiring neural-encoded data from the brain 12 by using a single fixed source-detector arrangement to create one optical path 14 through the brain 12 in a single measurement period, in a practical implementation capable of localizing the fast-optical signal an x-y plane along the surface of the brain 12, variations of the optical measurement system 10 may utilize more complex source-detector arrangements (e.g., single-source multi-detector, multi-source single-detector, or multi-source multi-detector) to simultaneously create multiple optical paths 14 spatially separated from each other within brain 12 in a single measurement period, or may utilize a movable source-detector arrangement to sequentially create multiple optical paths 14 over several measurement periods, as described in U.S. patent application Ser. No. 16/379,090, entitled "Frequency Domain Optical Spectroscopy For Neural Decoding," and U.S. Provisional patent application Ser. No. 16/392,963, entitled "Interferometric Frequency-Swept Source and Detector in a Photonic Integrated Circuit," which are expressly incorporated herein by reference. Thus, in a practical implementation, the optical detection system 10 may detect and localize physiological activity associated with neural activity in the brain, including fast-optical signals, in three-dimensions, with two of the dimensions represented as an x-y plane spanning the surface of the brain 12 encoded within the spatially separated multiple optical paths 14 and the third dimension (z-dimension or depth into the brain 12) being encoded within a time-of-flight (TOF) profile of photons propagating along the optical paths 14.

The optical measurement system 10 generally comprises an optical source assembly 20, an optical detector assembly 22, a controller 24, and a processor 26, which operate together to non-invasively distinguish between a plurality of states of a fast-optical signal in the brain 12. In this embodiment, only a single source-detector arrangement is described, although as briefly discussed above, the optical measurement system 10 may employ a complex source-detector arrangement.

The optical source assembly 20 is configured for generating and delivering sample light 28 into the brain 12. In the preferred embodiment, the optical source assembly 20 emits the sample light 28 at a fixed pulse frequency, pulse duration, and pulse intensity, although in alternative embodiments, the optical source assembly 20 may comprise control inputs for receiving control signals from the controller 24 that instruct the optical source assembly 20 to emit the sample light 28 at a selected time, duration, and intensity. In the preferred embodiment, the controller 24 instructs the optical source assembly 20 to emit relatively short optical pulses, as will be described in further detail below.

The sample light 28 travels along the optical path 14, such that the sample light 28 scatters diffusively through the brain 12, and back out again, exiting as signal light 30. As it scatters diffusively through the brain 12, various portions of the sample light 28 will take different paths through the brain 12. For purposes of brevity, only a first sample light portion 40a traveling along a relatively long path, and a second sample light portion 40b traveling along a relatively short path, are illustrated, although it should be appreciated that the diffused sample light 28 will travel along many more paths through the brain 12.

The sample light 28, and thus the signal light 30, may be ultraviolet (UV) light, visible light, and/or near-infrared and infrared light, and may have any suitable wavelength, e.g., in the range of 350 nm-1800 nm. The sample light 28 may be close to monochromatic in nature, comprising approximately a single-wavelength light, or the sample light 28 may have multiple wavelengths (e.g., white light or ultrashort pulse). In some variations, the sample light 28 may have a broad optical spectrum or may have a narrow optical spectrum that is then rapidly swept (e.g., changed over time) to functionally mimic or create an effective broad optical spectrum.

Notwithstanding the foregoing, it is preferred that the optical wavelength of the sample light 28 be selected to maximize sensitivity to the specific physiological activity of interest. For example, in the preferred case where the physiological activity of interest is the presence of a fast-optical signal, an optical wavelength greater than 850 nm may be used for the sample light 28. Optionally, an optical wavelength equal to or greater 1000 nm may be used for the sample light 28 to maximize penetration. In the additional or alternative case where the physiological activity of interest is a change in the blood oxygen concentration, an optical wavelength in the range of 650 nm to 750 nm may be used for the sample light 28. Multiple optical wavelengths can be used for the sample light 28 to allow different physiological activities to be distinguished from each other. For example, sample light 28 having two optical wavelengths of 900 nm and 700 nm can be respectively used to resolve fast-optical signals and blood oxygenation. Alternatively, the wavelength of the sample light 28 to be selected to maximize the detector sensitivity.

Significantly, the signal light 30 will be encoded with any neurological events (and alternatively any hemodynamic events) that change an optical property of tissue within the brain 12. To this end, the optical detector assembly 22 is configured for detecting the neural-encoded signal light 30 and generating a neural-encoded electrical signal from which one of a plurality of different states of the fast-optical signal in the brain 12 can be identified by the processor 26, as will be described in further detail below. It should be appreciated that, although not all of the sample light 28 from which the signal light 30 is derived passes through the brain 12 and is detected, it is only important that at least some of the signal light 30 exiting the brain 12 be detected. The optical detector assembly 22 comprises control inputs for receiving control signals from the controller 24 that allow the optical detector assembly 22 to detect the signal light 30 within the measurement period.

Although the controller 24 and processor 26 are described herein as being separate components, it should be appreciated that portions or all functionality of the controller 24 and processor 26 may be performed by a single computing device. Furthermore, although all of the functionality of the controller 24 is described herein as being performed by a single device, and likewise all of the functionality of the processor 26 is described herein as being performed by a single device, such functionality each of the controller 24 and the processor 26 may be distributed amongst several computing devices. Moreover, it should be appreciated that those skilled in the art are familiar with the terms "controller" and "processor," and that they may be implemented in software, firmware, hardware, or any suitable combination thereof.

Figure 2:
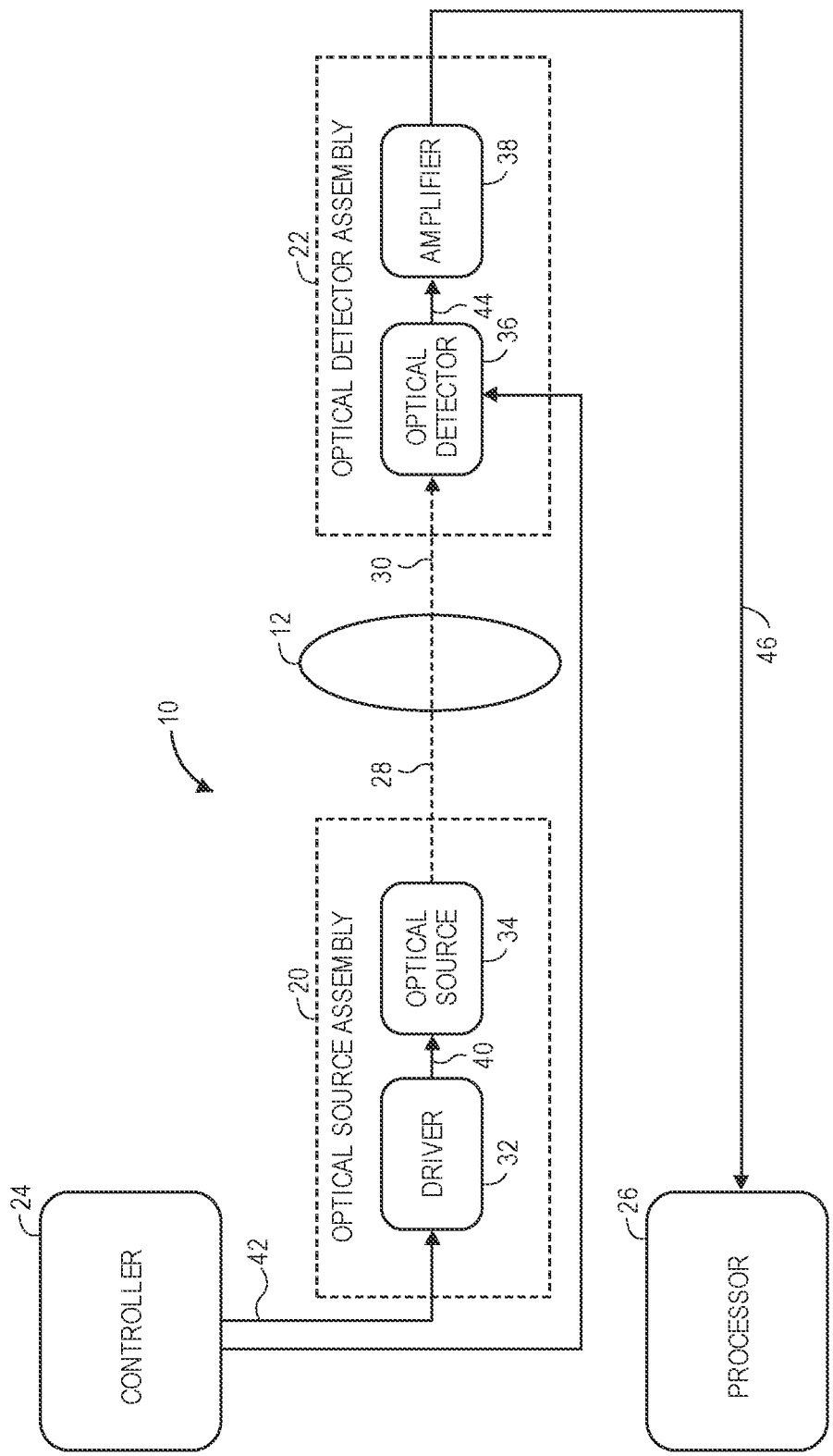
FIG. 2 is a detailed block diagram of the optical measurement system of FIG. 1.

Referring now to FIG. 2, the optical source assembly 20 comprises an optical source driver 32 configured for outputting a drive signal 40, and an optical source 34 configured for outputting the sample light 28 in accordance with the drive signal 40. The sample light 28 may then be delivered into the brain 12, which is scattered as the neural-encoded signal light 30 that exits the brain 12, as described above. The optical source driver 32 may receive control signals 42 from the controller 24 (either analog or direct digital synthesis inputs) for controlling the characteristics of the drive signal 40, including the intensity and timing of the pulses of the sample light 28. Optionally, a direct current (DC) offset (not shown) can be applied to bias the optical source 34 to allow it to more quickly turn on and off. Optionally, the optical source 34 may have additional outputs (e.g., for monitoring temperature or pulse timing (trigger output).

The optical detector assembly 22 comprises an optical detector 36 configured for detecting the exiting neural-encoded signal light 30 and outputting an electrical neural-encoded signal 44 representative of the signal light 30; and an amplifier 38 configured for amplifying the electrical neural-encoded signal 44 and outputting an amplified neural-encoded signal 46, which can be pre-conditioned and analyzed by the processor 26, as discussed in further detail below. In the case where analog processing of the electrical neural-encoded signal light 30 is performed, as will be discussed in further detail below, the amplifier 38 may be, e.g., a trans-impedance amplifier (TIA) to impedance match the optical detector 36 to the analog circuitry, reducing the effects of detector electronic Johnson noise and enabling a photon shot noise limited measurement of the neural-encoded signal light 30.

Advantageously, because the optical measurement system 10 does not utilize holography, in addition to not requiring complex and expensive equipment, the optical measurement system 10 does not require the detection of speckles (i.e., the use of highly coherent light and the ability to spatially resolve speckles at the detection plane). As such, the optical source 34 may take the form of a very simple and inexpensive component, such as a vertical-cavity surface-emitting laser (VCSEL), a light emitting diode (LED), an edge emitting diode laser, a flash lamp, etc. Preferably, the optical source 34 is a high-coherence light source (i.e., a laser), although in alternative embodiments, the optical source 34 may be a low-coherence light source. To maximize collection of photons from the neural-encoded signal light 30, the optical detector 36 may be relatively large compared to camera pixels in holography systems, e.g., having an area greater than (30 $\mu$m)$^2$, or even an area greater than (200 $\mu$m)$^2$. Of course, the size of the optical detector 36 should be limited, e.g., less than (1000 $\mu$m)$^2$, such that the form factor of the optical measurement system 10 may be minimized, especially in the alternative embodiment where multiple optical detection assemblies 22 are utilized.

Alternatively, the optical detector 36 may comprise several discrete components to optimize bandwidth and increase sensitivity. Ultimately, the size of the optical detector 36 and number of discrete components that make up the optical detector 36 may be determined by the required number of photons captured during the measurement period due to the need to suppress shot noise and by the need to achieve fast photodetector bandwidths that operate in the GHz regime, e.g., sufficiently low capacitance (i.e., as the size of the optical detector 36 increases, it will have more capacitance, and will thereby have a slower response that will reduce its ability to measure the response, e.g., greater than 10 GHz).

Figure 3B:
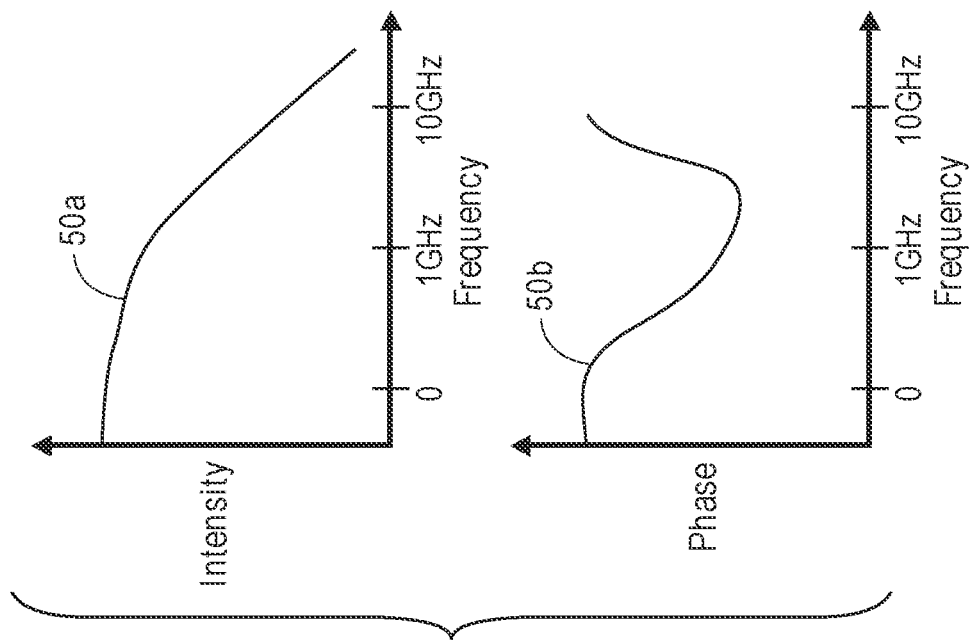
FIG. 3B is a frequency domain diagram of the intensity impulse response of FIG. 3A.
Figure 3A:
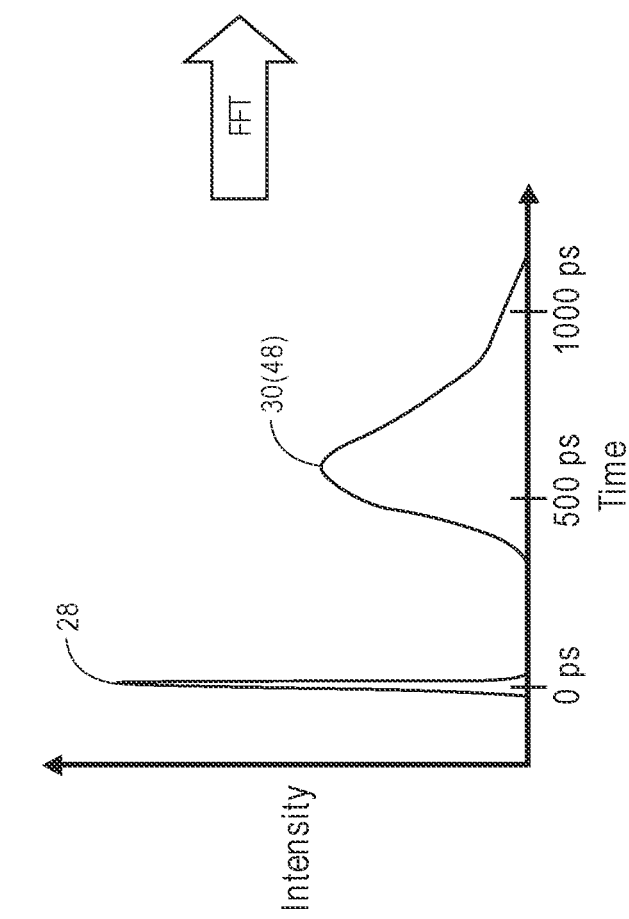
FIG. 3A is a time domain diagram of an intensity impulse response of signal light detected by the optical measurement system of FIG. 1 in response to the delivery of a sample light pulse.

In one advantageous embodiment, sample light 28 is delivered into the brain 12 by the optical source assembly 20 in the form of a relatively short optical pulse, which results in signal light 30 having a TOF profile 48 representing the different path delays of the photons within the neural-encoded signal light 30, as illustrated in FIG. 3A. The width of the optical pulse may be, e.g., less than 1 ns, and preferably less than 200 ps, but the optimum range is 50 ps or less. The width of the optical pulse may even be less than 1 ps if, e.g., fiber lasers are used. A Fast Fourier Transform (FFT), or other time-frequency transform, such as a wavelet transform, the detected signal light 30 resulting from the relatively short pulse of sample light 28 reveals that the detected signal light 30 carries intensity profile information 50a and phase profile information 50b over a broad frequency spectrum ranging from 0.1 GHz to 10 GHz, which inherently increases the sensitivity of any fast-optical signal encoded within the detected signal light 30, as illustrated in FIG. 3B. The pulse repetition rate of the optical source assembly 20 may be, e.g., from 100 MHz (fast enough to measure changes in the physiological activity corresponding to a minimum of 3 ns for the photons to escape or be absorbed by the anatomical structure 12).

In order to detect the full impulse response (i.e., the TOF profile 48) at a high resolution, it is preferred that the optical detector 36 have a very fast response time. To this end, the optical detector 36 preferable comprises a metal-semiconductor-metal (MSM) photodiode, which is a type III-V photodiode with increased quantum efficiency. MSM photodiodes are distinct from semiconductor photodiodes in that a metal-semiconductor (Shottky) contact is used, rather than junctions between different doped semiconductors. Thus, an MSM photodiode has a very fast response time, allowing measuring the shape of short light pulses in the many GHz bandwidth range, which lends itself well to measuring the signal light 30 resulting from the pulses of sample light 28 in the picosecond range. Alternatively, the optical detector 36 may take the form of a PIN photodiode, which has a detection speed on the order of an MSM photodiode.

Alternatively, other types of photodiodes, such as a semiconductor-based photodiode (e.g., silicon (Si) or indium gallium arsenide (InGaAs)), a single photon avalanche photodiode (SPAD) or avalanche photodiode (APD) that are operated in the linear or quasilinear regime, or other types of detectors, e.g., a charged couple device (CCD), or similar commercial-type image sensors, such as complementary metal-oxide-semiconductor (CMOS) sensor, can be used.

The optical detector 36 may obtain a high signal-to-noise (SNR) measurement of the TOF profile 48 within a single optical pulse of the signal light 30, rather than achieving the same SNR over many averages. Notably, electronic noise is present and the SNR decreases only by the square root of the number of light pulses when in the electronic limited, rather than photon shot noise limited, noise regime, where electronic noise from the detector is larger than photon shot noise because only a few photons fall on the detector from each pulse. Thus, the advantage of obtaining the high SNR TOF profile 48 from a single pulse, in contrast to averaging over a number of weaker pulses (for the same number of photons per second), is that once the photon shot noise limited regime is reached, then the SNR increases with the square root of the number of photons independently of whether or not multiple pulses are used, i.e., electronic noise becomes insignificant compared to photon shot noise.

Figures 4A, 4B:
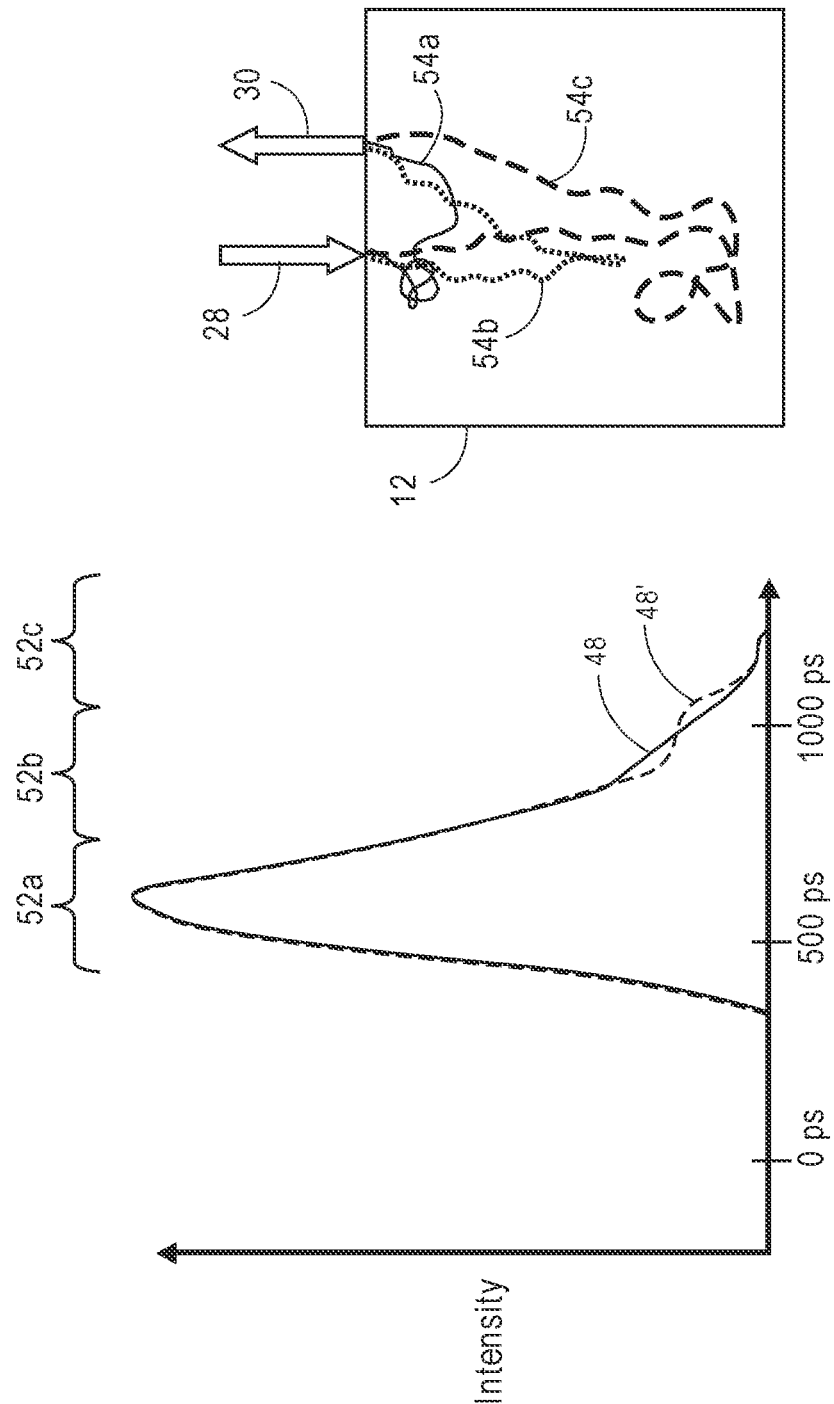
FIG. 4A is a time domain diagram of the intensity impulse response of FIG. 3A, particularly illustrating different time bins.
FIG. 4B is a diagram of different pathways of photons corresponding to the different time bins of the intensity impulse response of FIG. 4A.

Referring to FIG. 4A, it can be seen that there is a strong correlation between the depth of penetration of photons of the sample light 28 within the brain 12 and the shape of the waveform of the detected signal light 30 in the time domain. That is, the TOF profile 48 can be correlated to spatial depth information (i.e., the tail end of the TOF profile 48 contains relatively deep information, whereas the front end of the TOF profile 48 contains relatively shallow information), and thus, the spatial depth of the fast-optical signal along the optical path 14 (FIG. 1) may be determined. That is, it is known that the occurrence of the fast-optical signal along the optical path 14 will perturb the photons of the sample light 28 at the depth of the fast-optical signal along the optical path 14, thereby changing the intensity of the photons of the sample light 28 having an optical path length corresponding to that depth.

For example, as further illustrated in FIGS. 4A and 4B, a relatively early time-bin 52a of the TOF profile 48 contains more photons that travel a relatively short distance along the optical path 14; that is, photons 54a that penetrate superficially into the brain 12; a later time-bin 52b of the TOF profile 48 of the detected signal light 30 contains more photons that travel a relatively medial distance along the optical path 14; that is, photons 54b that penetrate further into the brain 12; and an even later time-bin 52c of the TOF profile 48 contains more photons that travel a maximum distance along the optical path 14; that is, photons 54c that penetrate even further and deeper into the brain 12.

Thus, it can be appreciated that the TOF profile 48 of the detected signal light 30 contains intensity-optical path length information in which the spatial depth of a fast-optical signal is encoded, and thus, a fast-optical signal that occurs at a certain depth in the brain 12 will cause a corresponding perturbation in the TOF profile 48. For example, as shown in FIG. 4A, there exists a perturbation between the baseline TOF profile 48 in the absence of a fast-optical signal, and a TOF profile 48' in the presence of a fast-optical signal. The fast-optical signal causes a measurable perturbation in the TOF profile 48 in time-bins 54b and 54c, indicating a change in scattering or absorption in the photons in the mid-level or maximum depth in the brain 12, and thus, a fast-optical signal at this depth in the brain 12.

Figure 5B:
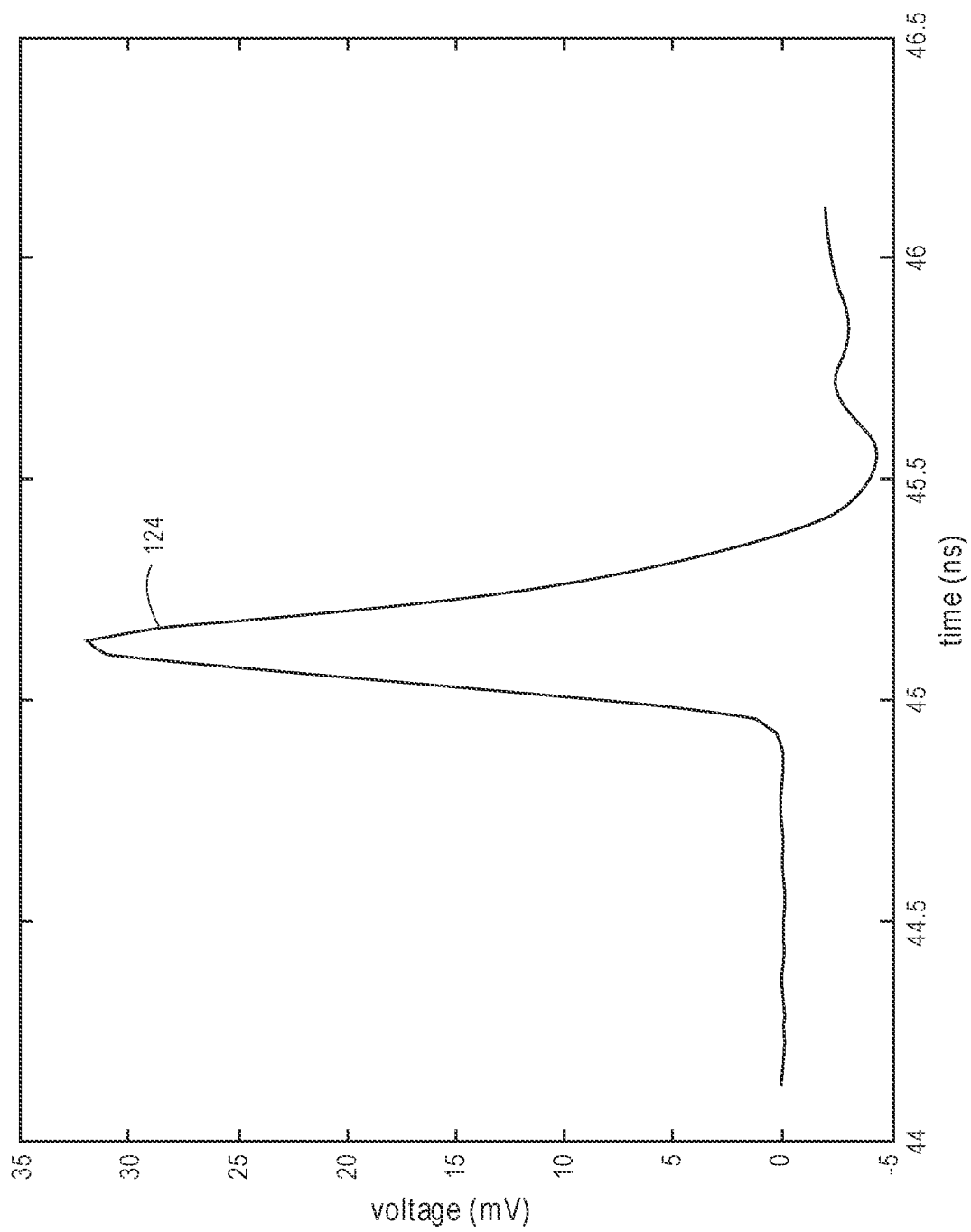
FIG. 5B is a time trace representing an intensity impulse response detected by the experimental optical detection system.

To prove the concept that a TOF profile can be directly extracted from a short pulse of light, an experimental optical detection system 100 was fabricated and tested, as illustrated in FIG. 5A. The experimental optical detection system 100 comprises a pulsed laser 102 (PicoQuant VisIR) that emits pulses of light 104 having an optical wavelength of 766 nm and a pulsewidth of approximately 120 ps, and at a repetition rate of 1 MHz. The light pulses 104 enter a tissue simulating phantom 106, where it scatters taking various optical paths within the tissue simulating phantom 106, and then exiting the tissue simulating phantom 106 as light pulses 108. The experimental optical detection system 100 further comprises a fast response photodiode 110 (MSM Hamamatsu photodiode (G4176-3)) that detects the light pulses 108, and outputs an electrical signal 112. The photodiode 110 is operated in the forward bias mode by a bias-T 114 (Tektronix PSPL5575A) and a DC power supply 116. The experimental optical detection system 100 further comprises an ultra-wideband radio frequency amplifier 118 (RF Lambda RLN01M10GA), which is also powered by the DC power supply 116. The amplifier 118 amplifies the electrical signal 112 and outputs an amplified electrical signal 120. The experimental optical detection system 100 further comprises a measurement device 122 (13 GHz Tektronix Infinium 90000 X-Series Scope) that measures the amplified electrical signal 120, and outputs a trace representing a TOF profile 124 of each detected light pulse 108, as illustrated in FIG. 5B.

Regardless of whether the TOF profile is acquired in an analog manner (e.g., the manner described above with respect to FIG. 3A) or in a digital manner, the optical measurement system 10 utilizes novel signal pre-conditioning and neural extraction techniques. Such novel pre-conditioning and neural extraction techniques described below can be implemented in the processor 26 illustrated in FIGS. 1 and 2. The challenges associated with attempting to extract a relatively small fast-optical signal from relatively noisy environment will be discussed with respect to a model that assumes that a head is illuminated with a short light pulse that produces a reflected light pulse (i.e., intensity impulse response) that can be measured in the time domain. The first portion of the reflected light pulse will only have traveled through the scalp and the skull and, therefore, does not contain useful information about neural activity in the brain. At a later time, a portion of the reflected light pulse will have traveled through brain tissue and, therefore, may be encoded with fast-optical signals. For purposes of analyzing the model in a simplified setting, it can be assumed that the number of photons of the reflected light pulse that did not reach the brain (i.e., the background light) are constant; the diffuse travel time of the photons that reached the cortex of the brain (i.e., the deep light) depends on neural activity; detection of the reflected light pulse is shot-noise limited; and the detector has an infinite dynamic range.

The TOF profile of the detected reflected light pulse can be modeled with a very simple model:

$$I(t) = \frac{I_{bg}}{\tau_{bg}} e^{-t/\tau_{bg}} + \frac{I_d}{\tau_{bg}\Gamma(1+\beta)} \left(\frac{t}{\tau_d}\right)^\beta e^{-t/\tau_d}, \quad [1]$$

where $I_{bg}$ is the total number of photons in the background light, $I_d$ is the total number of photons in the deep light, $\tau_{bg}$ is the time coefficient for the background light, $\tau_d$ is the diffuse travel time for the deep light, ß is a smoothing factor that determines how long it takes for the signal to reach a maximum and relates to the effective depth from which the deep photons arise, $\Gamma$ is a normalizing factor to ensure that the deep light of the TOF profile integrates to $I_d$. Note that $\tau_d > \tau_{bg}$, since the diffuse travel time of light that travels deep and contacts the brain 12 is, on average, longer than that which does not travel deep, and $\tau_d$ is time-dependent on the timescale of neural activity changes, i.e., milliseconds to seconds, due to the scattering changes comprising the fast optical signals. It should be appreciated that the model provided in equation [1] is for illustration purposes and in no way limits the invention, and although only a simple parametric model of TOF profile is used here (equation [1]), the same principles apply to more complex models that take into account the detailed geometry of the human head, tissue properties, time courses of fast-optical or other signals, removal of other signal components, such as blood oxygenation level-dependent (BOLD) signal or heart rate or motion related signals, use of physical simulators, or other modeling methods in the context analysis or implementation of pre-condition/analysis techniques used by the optical measurement system.

Figure 6:
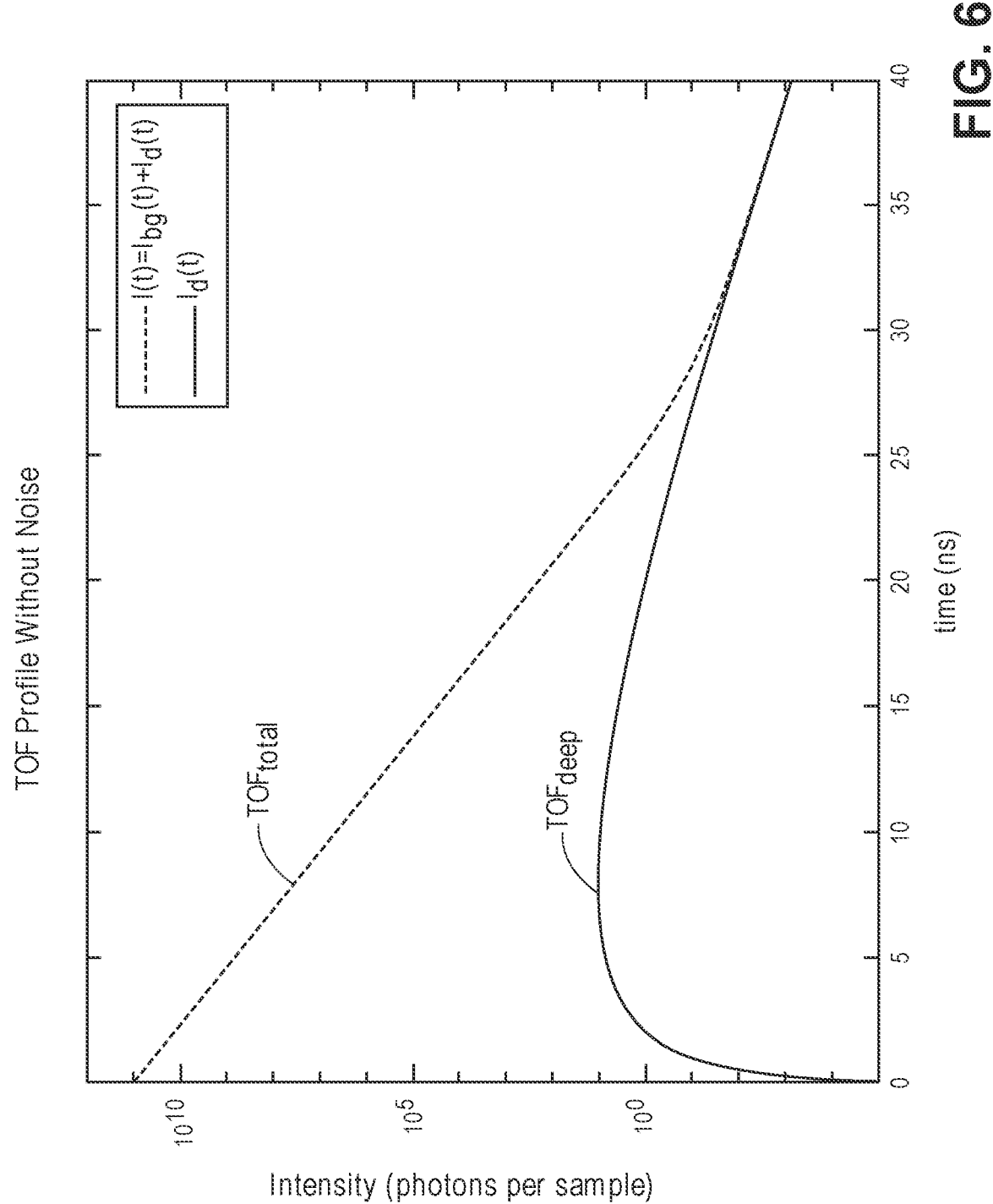
FIG. 6 is a time domain diagram illustrating a simulated TOF profile for all detected signal light exiting tissue versus a simulated TOF profile for only detected deep light exiting tissue, where such TOF profiles are simulated without shot noise.

Assuming $I_{bg}=10^{13}$, $I_d=10^4$, $\tau_{bd}=1$ ns, $\tau_d=2$ ns, and $\beta=4$, equation [1] can be computed to yield the TOF profile $TOF_{total}$ for all of the reflected light $I(t)=I_{bg}(t)+I_d(t)$ (i.e., the total estimated number of detected photons as a function of time). The deep light $I_d(t)$ contributes to a partial TOF profile $TOF_{deep}$ (i.e., the estimated number of deep photons as a function of time) can represented by the TOF profile 48, as shown in FIG. 6. As can be appreciated, there is a slow decay due to photons obtained at deeper depths within the brain, as shown by partial TOF profile $TOF_{deep}$ and a fast decay due to shallow photons, as shown by the TOF profile $TOF_{total}$, which includes deep photons, but is dominated by the photons obtained within shallow depths. It is desirable to determine the changes in the slow decay constant of $TOF_{deep}$ as an indicator of a fast-optical signal (neural activity). As can also be appreciated, it is very difficult to distinguish small changes in $TOF_{deep}$ for the deep light (where the fast-optical signal is encoded) in the context of a huge intensity of background light. The long-timescale convergence, i.e., height of the asymptote on the right part of the curve (which is indicative of the difference in long-scale decay time between different states (in this case, $\tau_d=2.0$ ns and $\tau_d=2.1$ ns) is comparable to the information obtained from the conventional FD-NIRS technique, whereby the height of this asymptote is on the order of one or a few picoseconds, which is similar to the conventional FD-NIRS observed average diffuse delay time difference.

Figure 7:
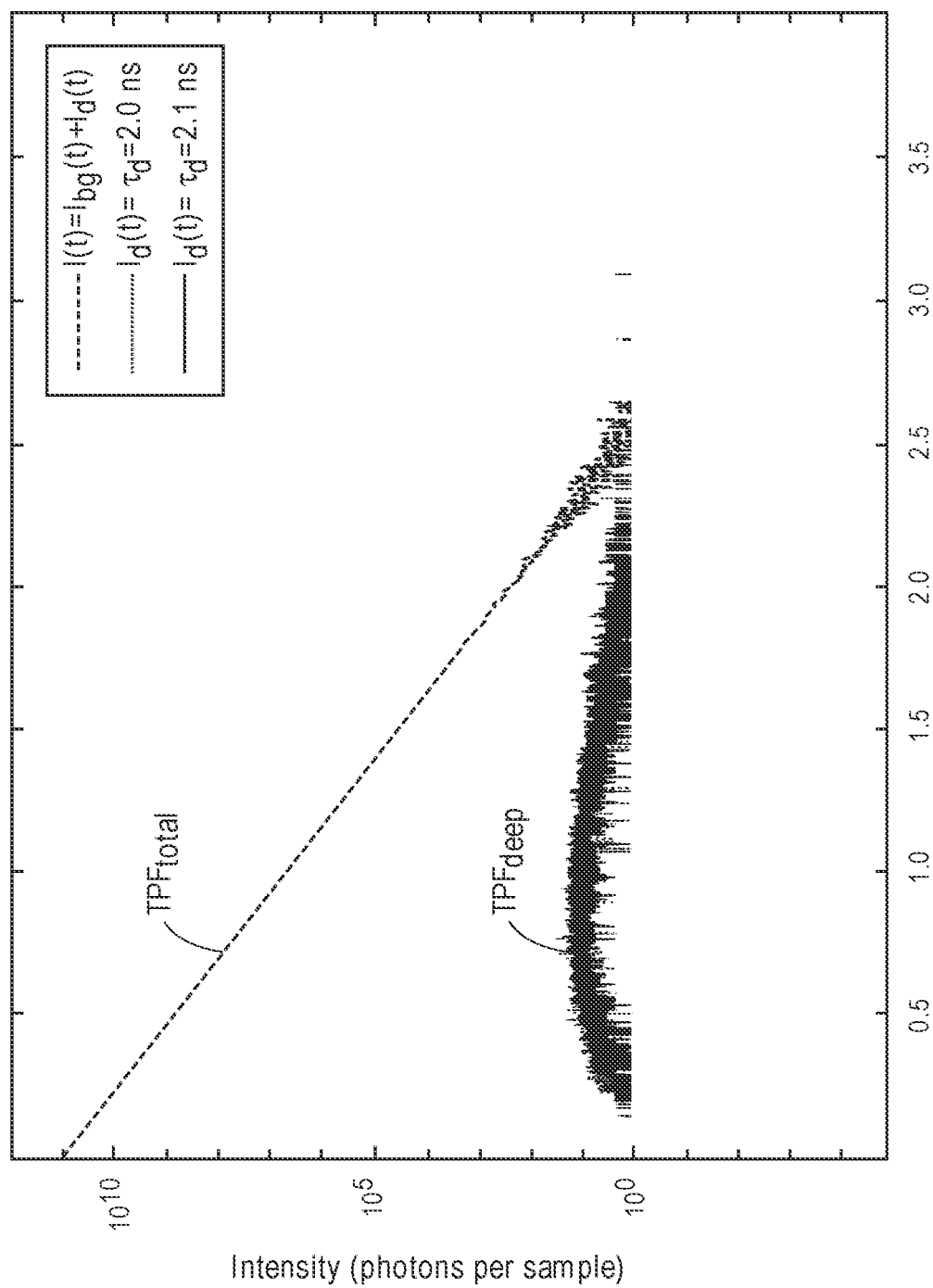
FIG. 7 is a time domain diagram illustrating a simulated TOF profile for all detected signal light exiting tissue versus a simulated TOF profile for only detected deep light exiting tissue, where such TOF profiles are simulated with shot noise.

When optical shot noise is taken into account, which can be added to equation [1] by sampling from a Poisson distribution at each histogram bin, for example, using the poissrnd function of Matlab, with the bin values illustrated in $TOF_{total}$, $TOF_{deep}$ of FIG. 6 assumed to be the mean for each bin, the task to effectively distinguish small changes in $TOF_{deep}$ for the deep light appears to be impossible. For example, as illustrated in FIG. 7, two different scattering states of the deep light (representing two different states of a fast-optical signal (active/inactive states or different active states) can be modeled, with shot noise, by varying the time coefficient $\tau_d$ of the deep light, and in this case, between $\tau_d=2.0$ ns and $\tau_d=2.1$ ns. As can be appreciated from FIG. 7, the two scattering states would be very difficult to distinguish from each other, since fast-optical signals only lead to small changes in the bin occupancy of the TOF profile. Therefore, clever analysis techniques are needed to distinguish between two states of a fast-optical signal.

As can be appreciated in FIG. 6, it is clear that most of the light pulse delivered into the head is reflected or back-scattered off of the scalp and skull, and therefore does not contain any useful information about fast-optical signals. Unfortunately, this background light does contribute to shot noise, possibly swamping the much weaker signal in the deeper light $I_d(t)$. Intuitively, it makes sense to discard the first part of $TOF_{total}$, because it mainly contains the background signal. However, the maximum of the deeper light $I_d(t)$ also occurs relatively early, raising the issue of which portion of $TOF_{total}$ should be discarded. Thus, the shape/slope prior to the long term right asymptote of $TOF_{total}$ illustrated in FIG. 6 contains useful information relevant to distinguishing states of a fast-optical signal.

Figure 8:
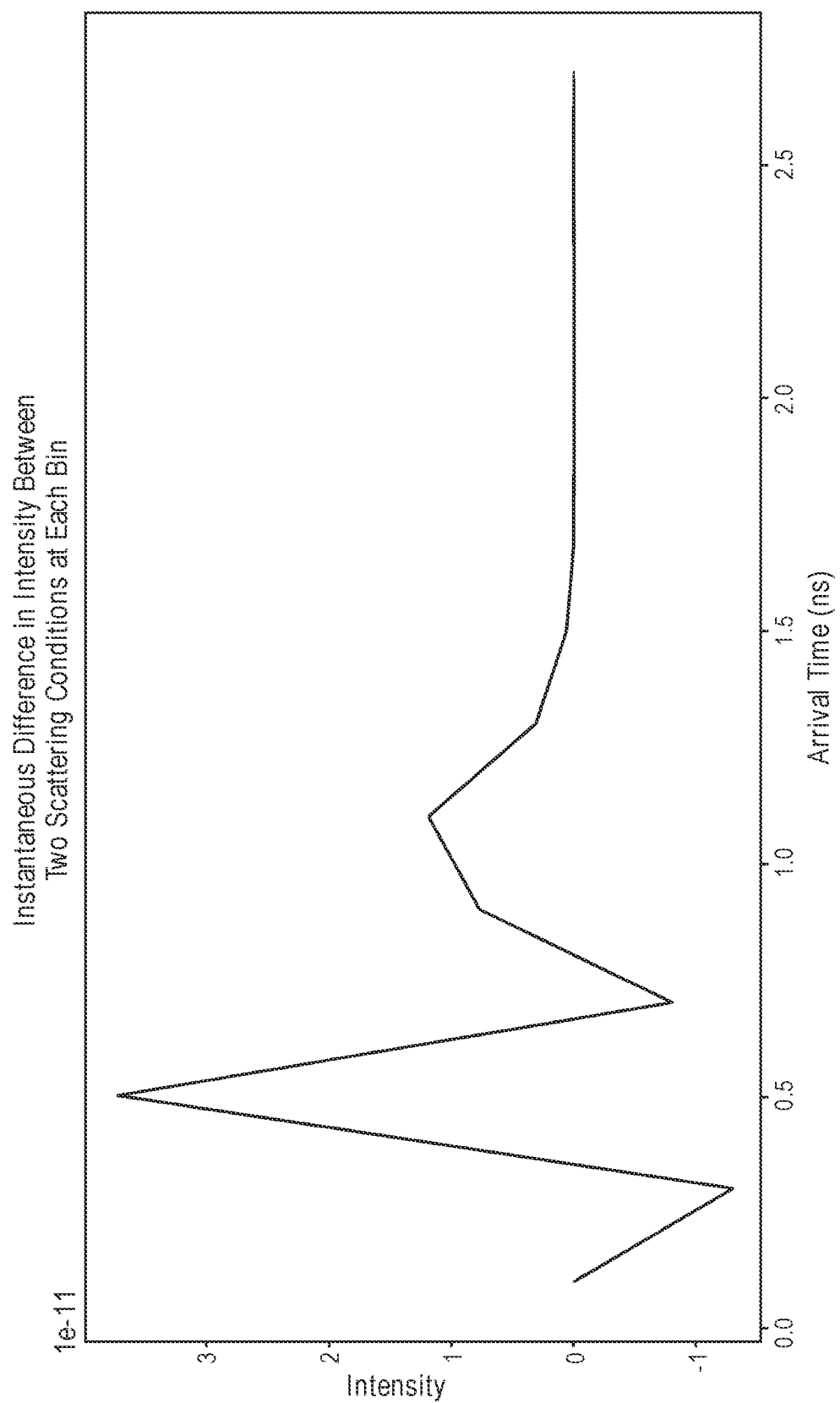
FIG. 8 is a time domain diagram illustrating an intensity of instantaneous differences between simulated detected deep light having two scattering conditions.
Figure 9:
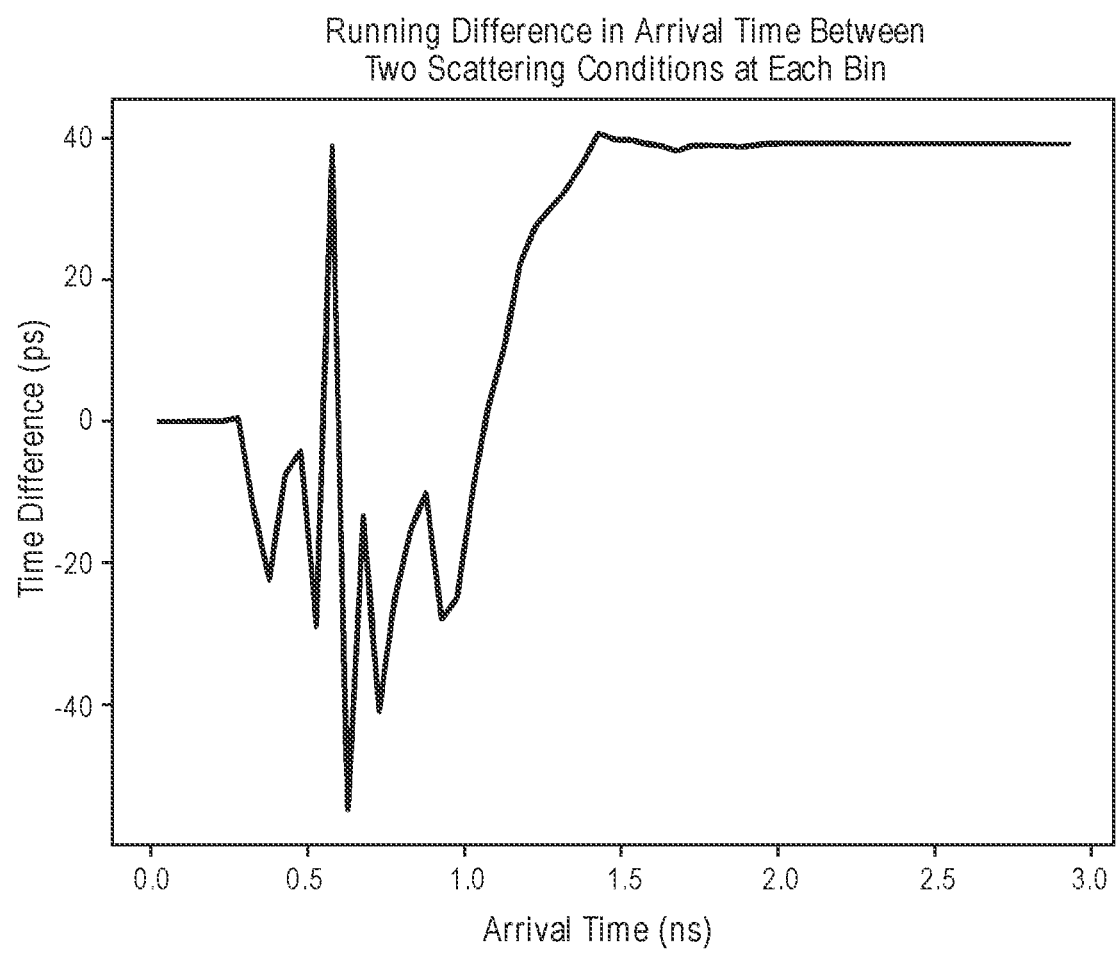
FIG. 9 is a time domain diagram illustrating a running time of arrival difference between simulated detected deep light having two scattering conditions.

For example, with reference to FIG. 8, a Monte Carlo simulation can be performed on brain tissue with two scattering conditions (a low scattering condition ($\mu_s=20.5$) and a high scattering coefficient ($\mu_s=22.5$)) to generate two TOF profiles that can then be subtracted from each other to reveal a bin-by-bin difference in intensity (in arbitrary units (AU)) that mimics a fast-optical signal in simulation. As further illustrated in FIG. 9, the difference in mean arrival time (centroid) of the TOF profiles with and without a small scattering change ($\mu_s=22.5$ versus $\mu_s=20.5$), computed after varying total amounts of elapsed time, shows how the differences in the expected diffuse travel time emerges over time as the pulse is integrated over time. Large effects in the cumulative time of flight difference between the TOF profiles are seen between 0.5 ns and 1.5 ns in this simulation, after which the effect stabilizes.

In contrast to analyzing a TOF profile to merely obtain the diffuse time delay, which corresponds to only knowing the long term right asymptote of $TOF_{total}$ illustrated in FIG. 6, and which is the characteristic of the $TOF_{total}$ that can be detected by the conventional FD-NIRS technique, the optical measurement system 10 is capable of analyzing the precise shapes/slopes at multiple point of $TOF_{total}$ prior to its long term asymptote, which contains useful information relevant to distinguishing states of a fast-optical signal.

Even in the extreme case exemplified in FIG. 7, the optical measurement system 10 uses clever techniques to distinguish between two different states of a fast-optical signal in the presence of a huge background noise by pre-conditioning the TOF profile in a manner that greatly increases the CNR of the fast-optical signal, and then analyzing the pre-conditioned TOF profile at a high resolution, facilitated by the rapidly-sampled high-bandwidth detection of the TOF profile of the signal light described above. Furthermore, as discussed above, the optical measurement system 10 is sensitive to these effects in the TOF profile by using a high band-width (at least a few GHz) detection.

In one advantageous implementation, the optical measurement system 10 pre conditions a TOF profile by weighting the TOF profile in a manner that decreases the variance of shot noise over the TOF profile. The standard deviation of the shot noise of a signal $I(t)$ at a given temporal time-of-flight bin centered on time t is equal to $\sqrt{I(t)}$. If we were to divide the signal by $\sqrt{I(t)}$, this would cause the standard deviation of the noise of the signal to equal ~1. Such division is equivalent to taking the square root of the signal itself. Thus, shot noise variance changes across bins may be minimized by applying a square root to the TOF profile in accordance with the equation:

$$A(t) = \sqrt{I_{measured}(t)}, \qquad [2]$$

where A(t) is the pre-conditioned TOF profile and I(t) is the detected TOF profile. It should be appreciated that the detected TOF profile I(t) can also be equivalently be divided by the square root of the detected TOF profile I(t) to acquire the pre-conditioned TOF profile A(t). This square root pre-conditioning of the TOF profile, such that all samples (or bins) have approximately the same effective noise level, increases the downstream analysis sensitivity to noise. Alternatively, fractional powers besides ½ can be applied to the TOF profile, e.g., ⅖ or ⅓, or the generalized Anscombe Transform function may be applied to the TOF profile to minimize the variance of the shot noise in the TOF profile. Moreover, if the short-term or long-term average of the quantity $\sqrt{I(t)}$ is known, denoted $\langle\sqrt{I(t)}\rangle$ for instance by averaging measurements over several pulses or TOF curve acquisitions, a version of the pre-conditioning may be obtained by dividing I(t) by $\langle\sqrt{I(t)}\rangle$. This version is more robust to situations in which very few photons are collected in a given bin on a given measurement. This version applies in situations where $\sqrt{I(t)}$ remains relatively close to the short term or long term temporal average $\langle\sqrt{I(t)}\rangle$ so that this average can be used as a proxy for the actual value; thus, the computation of the average may need to be repeated frequently in order to maintain it as a reliable estimate.

The optical measurement system 10 may additionally pre-condition a TOF profile by truncating all data points of the TOF profile prior to the time to in accordance with the equation, which also includes the square root based pre-conditioning:

$$A(t) = \sqrt{I_{measured}(t)\Theta(t-t_0)}, \quad [3]$$

where $\Theta$ denotes a "step function." This is especially useful to prevent saturation of the detector or amplifier by the initial portion of the signal $I_{measured}(t)$. Combinations of such truncation and the other versions of the square root preconditioning described below are also assumed here.

After pre-conditioning the TOF profile, the optical measurement system 10 utilizes one of several neural activity extraction techniques to distinguish between different states of the fast-optical signal by reducing the pre-conditioned TOF profile to a single neural-encoded value representing an intensity index of the neural activity.

For example, in one neural activity extraction technique, the optical measurement system 10 employs a "centroid computation" technique that computes the centroid of the pre-conditioned TOF profile in accordance with the equation:

$$\tau = \frac{\int A(t)*t\,dt}{\int A(t)\,dt}, \quad [4]$$

where A(t) is the intensity of the pre-conditioned TOF profile, $\tau$ is the diffuse delay time (i.e., centroid), and t is time of flight. In this case, the diffuse delay time T represents the intensity index of the fast-optical signal (or neural activity) encoded within the detected TOF profile.

In another neural activity extraction technique, the optical measurement system 10 employs an "active/inactive fitting" technique that compares the pre-conditioned TOF profile to a reference active TOF profile (i.e., a TOF profile generated in the presence of a fast-optical signal) and a reference inactive TOF profile (i.e., TOF profile generated in the absence of a fast-optical signal) to respectively compute active state and inactive state correlation coefficients, and based on these correlation coefficients, computing a neural activity index.

$$C_a = A_{active} \cdot A_t \quad [5]$$

$$C_i = A_{inactive} \cdot A_t \quad [6]$$

$$\alpha = \frac{C_a - C_i}{C_a + C_i} \quad [7]$$

where $A_t$ is the intensity of the pre-conditioned TOF profile, $A_{active}$ is the intensity of the reference active pre-conditioned TOF profile, $A_{inactive}$ is the intensity of the reference inactive pre-conditioned TOF profile, $C_a$ is the active state correlation coefficient, $C_i$ is the inactive state correlation coefficient, "·" is a dot product operator, and $\alpha$ is a value representing the intensity index of the fast-optical signal (or neural activity) encoded within the detected TOF profile.

In still another neural activity extraction technique, the optical measurement system employs a "singular value decomposition (SVD)" technique. In particular, a SVD gives the average behavior (in the singular vector with the highest singular value) and the most "discriminating" curve (in the singular vector with the second highest singular value). Calculating the dot product of the TOF profile with the most discriminating vector gives an index of the measured brain activity.

$$C_1 = A_{sv1} \cdot A_t \quad [8]$$

$$C_2 = A_{sv2} \cdot A_t \quad [9]$$

$$\alpha = \frac{C_1 - C_2}{C_1 + C_2} \quad [10]$$

Significantly, it can be demonstrated that pre-conditioning a TOF profile, when used in conjunction with these neural activity extraction techniques, yields remarkably improved sensitivity to fast-optical signals compared to the state of the art, e.g., approximately three orders of magnitude more efficient in SNR compared to conventional FD-NIRS. Regardless of the technique used to acquire a TOF profile; albeit using an analog manner, which detects the full "intensity impulse response," as discussed above; or in a more conventional manner digital manner (e.g., techniques used by SPAD, iNIRS, and others) that yields an approximation of that response (i.e., a histogram of the photon arrival times binned with a certain time resolution, such as 100 ps, 30 ps, 500 ps, 1 ns, etc.); or by equivalently taking frequency domain measurements that effectively comprise the Fourier transform of such intensity impulse response, and thus can be used, via the inverse Fast Fourier transform (IFFT), to reconstruct the intensity impulse response, as described in U.S. patent application Ser. No. 16/379,090, entitled "Frequency Domain Optical Spectroscopy For Neural Decoding," which is expressly incorporated herein by reference, the TOF pre conditioning and analysis techniques described above can be used to maximize the sensitivity in identifying a fast-optical signal within a TOF profile.

The sensitivity of various combinations of the TOF pre-conditioning techniques and TOF analysis techniques, as well as the conventional FD-NIRS technique, to fast-optical signals were explored by computing equation [1], assuming $I_{bg}=10^{13}$, $I_d=10^4$, $\tau_{bd}=1$ ns, $\beta=4$ and $\tau_d$ ranging from 1.8 ns to 2.2 ns in steps of 0.01 ns, while adding Poisson noise to each bin using the poissrnd function in Matlab, to acquire TOF profiles (one for each value of $\tau_d$). Each pre-conditioning/analysis technique was then applied to each TOF profile to extract the index value of the fast-optical signal intensity, which can be plotted over the range of $\tau_d$ values (which strongly correlate to the intensity of the fast-optical signal, and therefore, also serve as index values for the fast-optical signal intensity). Each set of extracted index values was then fitted to a line to determine the extent to which the respective set of extracted index values is linearly correlated with the actual change in the neural activity dependent parameter, thereby providing an intrinsic measure of the sensitivity of each pre-conditioning/analysis technique to fast-optical signals. Fit quality in each case was evaluated by computing the Pearson correlation coefficient ($R^2$ value) between each set of extracted values (measured values) and the of $\tau_d$ values (actual values). Such $R^2$ values are provided in the table below, with the higher values being better, and a value of 1.0 indicating perfect correlation between the measured values and the actual values.

It should be noted that in a conventional FD-NIRS approach to fast-optical signal measurement, the detected intensity is:

$$\frac{1}{2} + \frac{1}{2}\cos\Omega t, \qquad [11]$$

rather than a short pulse. In contrast to the other approaches, which acquire the full "intensity impulse response" or an approximation of that response, the modulation/demodulation scheme in conventional FD-NIRS effectively samples a single frequency of the Fourier transform of a I(t) (i.e., a TOF profile). It should also be noted that the full conventional FD-NIRS technique was not simulated directly, but instead a single frequency component of the Fourier transform of I(t) was taken. The results obtained this way are most likely a factor of $\sqrt{2}$ better than with the prior art FD-NIRS approach, under ideal measurement conditions, because half of the energy in conventional FD-NIRS is contained in the constant DC offset of the measurement (i.e., the DC term in equation [11]) and contributes to shot noise. Although this offset carries no information relevant to the fast-optical signal, it does contribute to shot noise.

It should also be appreciated that the pre-conditioning and neural activity extraction techniques described herein are techniques that, in general, can uniquely be done in TOF-resolved approaches, therefore allowing for improved neural activity extraction by making use of the full TOF profile, but not in conventional FD-NIRS technique, which are unable to analyze TOF profiles, since their hardware setups do not obtain TOF profiles, and therefore, the mathematical equivalent of the absence of any pre-conditioning and the use of an average delay as the analysis metric of interest is effectively "baked in" intrinsically to their neural activity extraction techniques. Indeed, conventional FD-NIRS mathematically corresponds, in the best case, to computing the centroid of the full TOF profile directly without pre-conditioning, and in the worst case, to doing so in the context of a high noise background due to the DC constant offset or even worse with additional noise due to electronic aliasing effects or other non-idealities of the measurement system used in conventional FD-NIRS in practice. Despite this, the analysis here is generous to the conventional FD-NIRS approach in that it assumes the best case. Yet, a comparison between the pre-conditioning/neural activity extraction techniques employed by the optical measurement system 10 and the conventional FD-NIRS neural activity extraction technique (even with preconditioning), as set forth in Table 1 below, reveals that such novel pre-conditioning/neural activity extraction techniques methods out-perform even this generous treatment of conventional FD-NIRS. In this case, preconditioning of the TOF profiles were accomplished by computing the square root of each TOF profile and optionally truncating the first part of the respective TOF profile.

TABLE 1

(weak deep light ($I_d = 10^4$))

| Performance of Neural Activity Extraction Techniques With and Without Preconditioning | $R^2$ |
|---|---|
| FD-NIRS (low frequency) | 0.060778 |
| FD-NIRS (medium frequency) | 0.059991 |
| FD-NIRS (low frequency) | 0.031004 |
| Centroid | 0.061818 |
| Active/Inactive Fit | 0.00078828 |
| SVD | 0.049724 |
| FD-NIRS (low frequency) with SQRT Pre-Conditioning | 0.096649 |
| FD-NIRS (medium frequency) with SQRT Pre-Conditioning | 0.076665 |
| FD-NIRS (high frequency) with SQRT Pre-Conditioning | 0.057307 |
| Centroid with SQRT Pre-Conditioning | 0.79287 |
| Active/Inactive Fit with SQRT Pre-Conditioning | 0.79712 |
| SVD with SQRT Pre-Conditioning | 0.79701 |
| FD-NIRS (low frequency) with SQRT/Truncation Pre-Conditioning | 0.44735 |
| FD-NIRS (medium frequency) with SQRT/Truncation Pre-Conditioning | 0.33008 |
| FD-NIRS (high frequency) with SQRT/Truncation Pre-Conditioning | 0.036542 |
| Centroid with SQRT/Truncation Pre-Conditioning | 0.79734 |
| Active/Inactive Fit with SQRT/Truncation Pre-Conditioning | 0.79701 |
| SVD with SQRT/Truncation Pre-Conditioning | 0.79703 |
| Perfect Fit | 1.00000 |

In order to test the accuracy of the modeling, an extremely strong deep light ($I_d=10^{10}$) was assumed for equation [1]. As shown in Table 2, all techniques yield very accurate results.

TABLE 2

(extremely strong deep light ($I_d = 10^{10}$))

| Performance of Neural Activity Extraction Techniques With and Without Preconditioning | $R^2$ |
|---|---|
| FD-NIRS (low frequency) | 0.96981 |
| FD-NIRS (medium frequency) | 0.99254 |
| FD-NIRS (low frequency) | 0.97946 |
| Centroid | 1.00000 |
| Active/Inactive Fit | 0.99837 |
| SVD | 0.99839 |
| FD-NIRS (low frequency) with SQRT Pre-Conditioning | 0.98919 |
| FD-NIRS (medium frequency) with SQRT Pre-Conditioning | 0.97827 |
| FD-NIRS | 0.90833 |
| Centroid with SQRT Pre-Conditioning | 0.99983 |
| Active/Inactive Fit with SQRT Pre-Conditioning | 0.99942 |
| SVD with SQRT Pre-Conditioning | 0.99942 |
| FD-NIRS (low frequency) with SQRT/Truncation Pre-Conditioning | 0.99756 |
| FD-NIRS (medium frequency) with SQRT/Truncation Pre-Conditioning | 0.99972 |
| FD-NIRS (high frequency) with SQRT/Truncation Pre-Conditioning | 098349 |
| Centroid with SQRT/Truncation Pre-Conditioning | 0.99985 |
| Active/Inactive Fit with SQRT/Truncation Pre-Conditioning | 0.99942 |
| SVD with SQRT/Truncation Pre-Conditioning | 0.99942 |
| Perfect Fit | 1.00000 |

It can be seen from Table 1 that pre-conditioning a detected or derived TOF profile with a fractional power, and in this case a square root, to equalize the shot noise, dramatically increases the accuracy of the centroid, active/inactive fitting, and SVD fitting neural activity extraction techniques in a very unexpected manner in that they are near-optimal from the perspective of accurate neural activity dependent parameter determination, whereas the FD-NIRS neural activity extraction technique appears to completely fail, and is thus, a poor way to distinguish between two fast-optical signal states (i.e., two states with different amounts of scattering). The results in Table 1 indicate that it is possible to accurately detect a variation in 10% in the diffusive arrival time of deep photons, even if there are only $10^4$ photons on a background of $10^{13}$ shallow photons. Thus, the pre-conditioning/neural activity extraction techniques employed by the optical measurement system 10 lead to a faster and more photon efficient system than that of state of the art fast-optical signal measurement approaches, such as FD-NIRS, and thus provides a differential advantage for measuring small signals inside the brain, such as naturally occurring fast-optical signals.

It should be noted that the simpler centroid neural activity extraction technique performs as well as the more complicated active/inactive and SVD neural activity extraction techniques. That is, whereas the active/inactive and SVD neural activity extraction techniques require reference active or inactive TOF profiles to be known prior to detecting TOF profiles, the centroid neural activity extraction technique does not require prior knowledge of any reference TOF profiles. Thus, the centroid neural activity extraction technique (with square root preconditioning) provides a simple and robust model-free method of acquiring a neural activity index from a TOF profile, and can be easily implemented in analog hardware as discussed in further detail below. It should also be noted that truncating the first 5 ns of a TOF profile does not appear to have a significant effect on improving the accuracy of any of the centroid, active/inactive, and SVD neural extraction techniques. However, truncating the first portion of TOF profile may prevent saturation of the detector or amplifier and thus may still be useful in practice.

In an optional embodiment, the optical measurement system 10 applies a weighting function to the TOF profile in a manner that further increases the contrast-to-noise ratio (CNR) of the TOF profile. In one embodiment, such weighting function can be a ramp function (e.g., a ramp function used in the centroid neural activity extraction technique described above) with or without the fractional power (e.g., square root) preconditioning, which equalizes the shot noise, ultimately increasing the CNR of the TOF profile. In one advantageous embodiment of the optical measurement system 10 that maximizes the CNR of the TOF profile, such weighting function comprises a previously known, measured, estimated, modeled or otherwise determined in intensity between two reference TOF profiles respectively corresponding to two states of the fast-optical signal (active/inactive states or two active states with different intensities) within the brain (i.e., a change in optical density) in accordance with the equation:

$$w(t)=dOD(t)=\Delta I(t)/I_0(t), \quad [12]$$

where $I_0(t)$ is the intensity of a first TOF profile (i.e., the TOF profile at the first state of the fast-optical signal), $I(t)$ is the intensity of a second TOF profile (i.e., the TOF profile at the second state of the fast-optical signal), and $\Delta I(t)=I(t)-I_0(t)$.

Assuming that $I(t)-I_0(t)<<I_0(t)$, a useful weighting function to maximize CNR for any scalar $\alpha$ can be given as:

$$w(t)=\alpha^* dOD(t)=\alpha^* dI(t)/I_0(t). \quad [13]$$

This weighting function has a higher CNR than weighting functions of 1) simple binning; 2) a temporal ramp function used in the centroid computation; and 3) the square root preconditioning combined with the temporal ramp function. CNR can be computed given a ratio of the change in optical density: $dOD(t)=\Delta I(t)/I_0(t)$ and the number of expected photons in a time bin under the baseline condition, $I_0(t)$. In this case, t refers to a time bin index, absolute contrast=$dOD(t)^*I_0(t)$, and the standard deviation of shot noise=$\sqrt{I(t)} \approx \sqrt{I_0(t)}$, given that $I(t)-I_0(t)<<I_0(t)$. It is also assumed here that $\Delta I(t)/I_0(t) \approx \log(I(t)/I_0(t))$.

In general, a weighted measure can be applied to a recorded TOF histogram $I(t)$ by applying a linear set of weights: $\Sigma_t w(t)I(t)$. The absolute contrast for this weighted measure would be:

$$C_M=\Sigma_t w(t)I(t)-\Sigma_t w(t)I_0(t)=\Sigma_t w(t)(I(t)-I_0(t))=\Sigma_t w(t)dOD(t)I_0(t). \quad [14]$$

The variance of the noise can be expressed as:

$$\sigma_M^2=\Sigma_t w^2(t)I_0(t), \quad [15]$$

and the standard deviation can thus be expressed as:

$$\sigma_M=\sqrt{\Sigma_t w^2(t)I_0(t)} \quad [16]$$

Thus, the generalized CNR may be expressed as:

$$CNR_M = \frac{C_M}{\sigma_M} = \frac{\sum_t w(t)dOD(t)I_0(t)}{\sqrt{\sum_t w^2(t)I_0(t)}} \quad [17]$$

$CNR_M$ can be equivalently formulated as:

$$CNR_M = \frac{a \cdot b}{\|a\|}, \quad [18]$$

where vector a with values is $w(t)\sqrt{I_0(t)}$, vector b with values is $dOD(t)\sqrt{I_0(t)}$, and "·" is the dot product. Given that the angle between two vectors can be defined as $$\cos\theta = \frac{a \cdot b}{\|a\|\|b\|},$$

then:

$$CNR_M=\|b\| \cos \theta. \quad [19]$$

In order to find the optimal set of weights $w_{opt}(t)$ to maximize $CNR_M$, only the term $\cos \theta$ can be varied, since the vector b is fixed and cannot be modified. The term $\cos \theta$ is maximized when $\theta=0$, i.e., $\alpha=\alpha b$. That is:

$$w_{opt}(t)\sqrt{I_0(t)}=\alpha dOD(t)\sqrt{I_0(t)} \Rightarrow w_{opt}(t)=\alpha dOD(t) \quad [20]$$

In comparison to the optimal weighting function for a TOF histogram, the weighting function used to compute a centroid of a TOF histogram can be determined as follows. The centroid measurement of a TOF histogram is:

$$C = \frac{\sum_t tI(t)}{\sum_t I(t)}, \quad [21]$$

which can be equivalently expressed as $C=\Sigma_t w_c(t)I(t)$, such that:

$$w_c(t) = \frac{t}{\sum_t I(t)}, \quad [22]$$

which is a ramp function. It should be noted that a centroid, as a measure, has a lower CNR than other direct weighting schemes, because the intensities are divided by the integral of the intensity. A simplified centroid measure without this normalization has higher contrast to noise values. Thus, the unnormalized weighting function can be:

$$w_c(t)=t. \quad [23]$$

The weighting function used to compute the square root of a TOF histogram can be determined as follows. The square root of a TOF histogram is:

$$A(t)=\sqrt{I(t)}, \quad [24]$$

which can be equivalently expressed as $A(t)=w_{pre}(t)I(t)$, such that:

$$w_{pre}(t) = \frac{1}{\sqrt{I(t)}}. \quad [25]$$

The combination of the unnormalized centroid weighting and the square root weighting yields:

$$w_c(t)*w_{pre}(t) = \frac{t}{\sqrt{I(t)}}. \quad [26]$$

To determine the CNRs using the optimal weighting function $w_{opt}(t)$, the simple centroid weighting function $w_c(t)$, and combined centroid square root weighting function $w_c(t)*ws_{qrt}(t)$, as well as various binning weighting functions, the relative contrast (or ratio of the change in optical density) $dOD(t)=\Delta I(t)/I_0(t)$ was first determined via a Monte Carlo simulation. The relative contrast dOD(t) was relatively similar between source-detector separations from 4-10 mm in a 5-layer model for a perturbation that is 20 mm×20 mm×2 mm, assuming a 1% absorption change, and thus, could be averaged to yield the mean relative contrast dOD(t) illustrated in FIG. 10. A baseline TOF profile $I_0(t)$ was obtained via human in-vivo data collection for each of various gates at 1 ps, 500 ps, 1000 ps, and 1500 ps, assuming a 9.8 mm source-detector separation. Assuming that for the standard deviation of the measurement $\sqrt{I(t)} \approx \sqrt{I_0(t)}$, and that the weights are the same for both I(t) and $I_0(t)$, the CNR using each of the optimal weighting function $w_{opt}(t)$, the simple centroid weighting function $w_c(t)$, and combined centroid square root weighting function $w_c(t)*w_{sqrt}(t)$, as well as various binning weighting functions (in this case, 500-1000 ps, 1000-1500 ps, 1500-2000 ps, and 1000-2000 ps), can be computed in accordance with equation [17].

Figure 10:
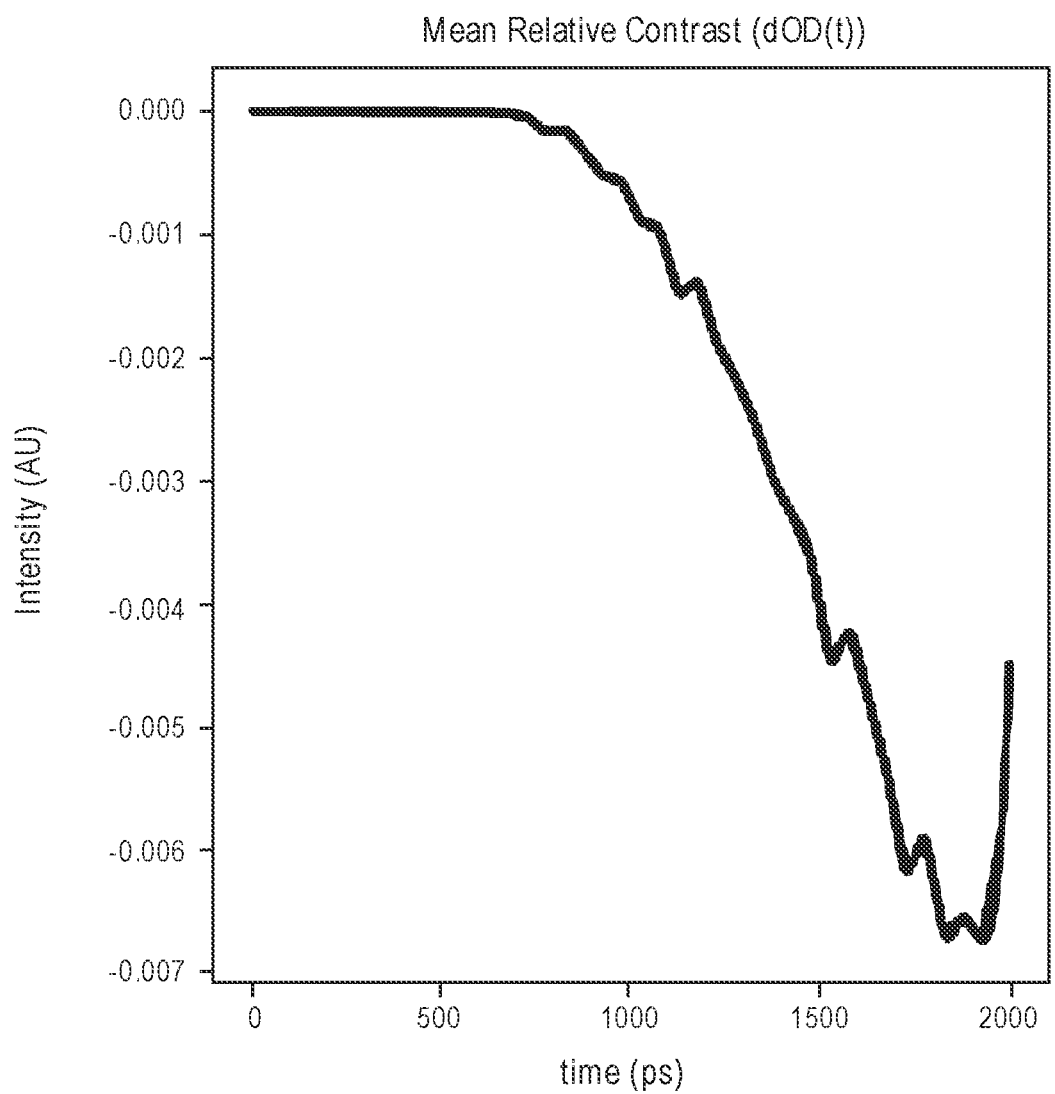
FIG. 10 is a time domain representation of the simulated signal change between a TOF profile from a baseline volume (I_0(t)) and a TOF profile from a volume with a 1% change in absorption coefficient in a cortical area (I(t))
Figure 11C:
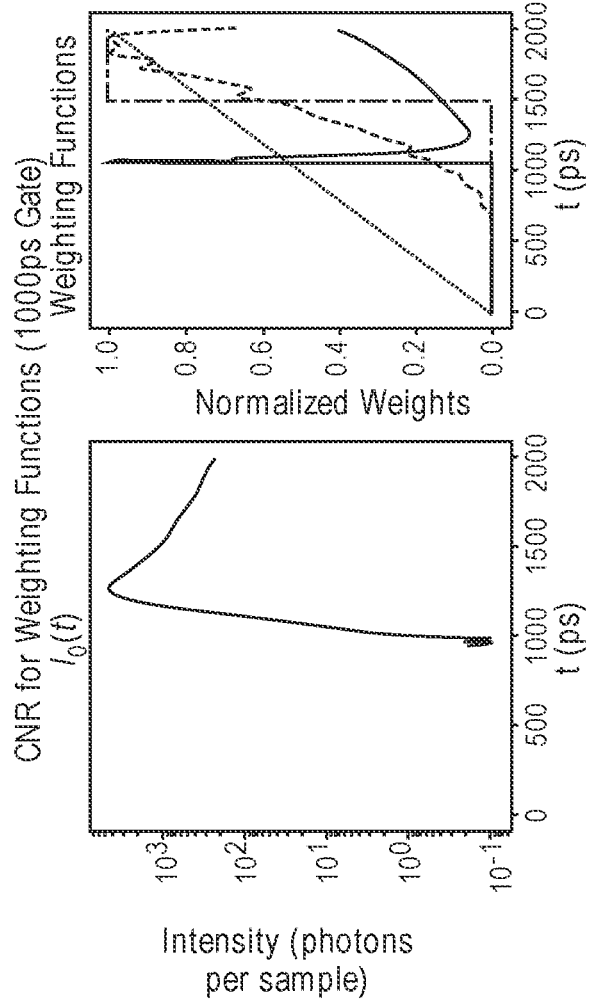
FIG. 11C is diagram illustrating a comparison of simulated weighting functions applied by the optical measurement system of FIG. 1 and a prior art system to an experimental TOF profile to increase the contrast to noise ratio (CNR) by applying a weighting function to a TOF profile, assuming a 1000 ps gate in the detection of the TOF profile.
Figure 11D:
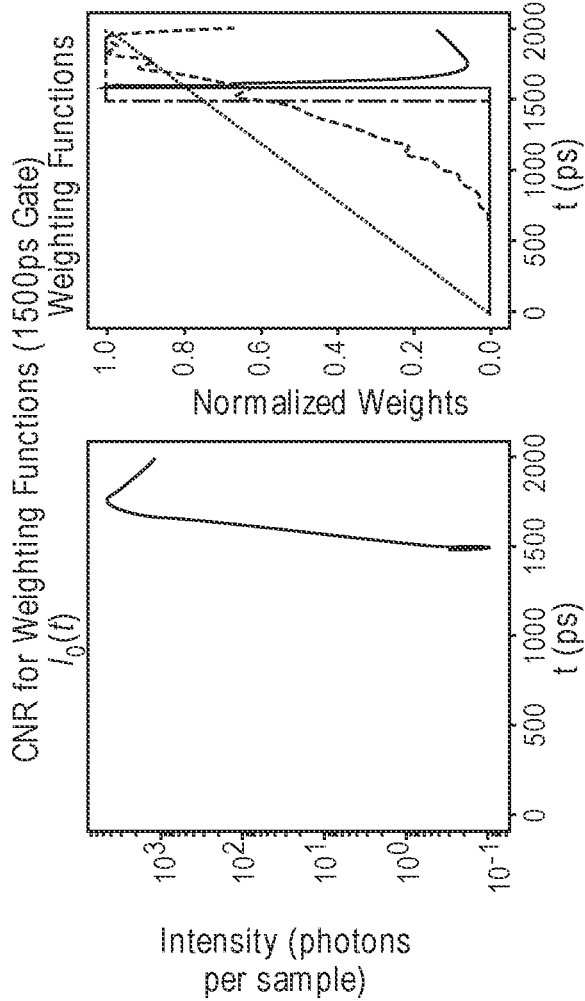
FIG. 11D is a diagram illustrating a comparison of simulated weighting functions applied by the optical measurement system of FIG. 1 and a prior art system to an experimental TOF profile to increase the contrast to noise ratio (CNR) by applying a weighting function to a TOF profile, assuming a 1500 ps gate in the detection of the TOF profile.

As illustrated in FIGS. 11A-11D, the various weighting functions were applied to the baseline TOF profiles with a 1 ps gate (FIG. 11A), 500 ps gate (FIG. 11B), 1000 ps gate (FIG. 11C), and 1500 ps (FIG. 11D), and using the relative contrast dOD(t) illustrated in FIG. 10. It can be seen that the optimal weighting function $w_{opt}(t)$ outperforms all of the other weighting functions. However, as can also be seen, the shape of the combined centroid square root weighting function approximates the shape of the optimal weighting function $w_{opt}(t)$, and based on this, its CNR is slightly less than the CNR associated with the optimal weighting function $w_{opt}(t)$. Thus, although the optimal weighting function $w_{opt}(t)$ outperforms the combined centroid square root weighting function, the combined centroid square root weighting function can be more conveniently implemented in hardware with the accompanying advantages, as discussed in further detail below.

As discussed above, a neural activity extraction technique (with pre-conditioning), and in the illustrated embodiment, the centroid neural activity extraction technique (with square root preconditioning), can be implemented in analog hardware to leverage the direct analog and rapidly-sampled high-bandwidth detection of the TOF profile. In this case, a portion of the processor 26 will be implemented in analog circuitry, whereas the remaining portion of the processor 26 will be implemented in digital circuitry (e.g., in a central processing unit (CPU)).

Figure 12A:
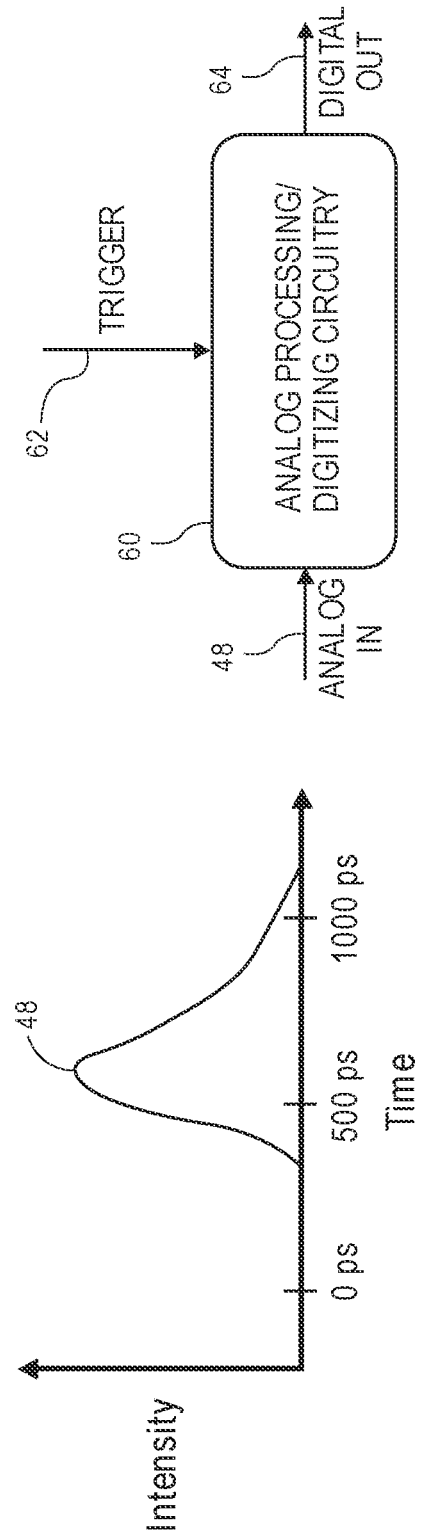
FIG. 12A is a block diagram of one embodiment of analog processing/digitizing circuitry that can be employed by the optical measurement system of FIG. 1 to directly detect and process a TOF profile in an analog manner.

In particular, and with reference first to FIG. 12A, one embodiment of generalized analog processing/digitizing circuitry 60 is configured for receiving the amplified neural-encoded signal 46 (i.e., the analog TOF profile 48) from the optical detector assembly 34 illustrated above in FIGS. 1 and 2, and, in response to a trigger signal 62 from the controller 24, reduces the analog TOF profile 48 to a single digitized index value 64 indicative of one of the two states of the fast-optical signal, which is output for delivery to the digital portion of the processor 26 for post-processing activity (e.g., determining the intensity and location of neural activity within the brain 12).

Figure 12B:
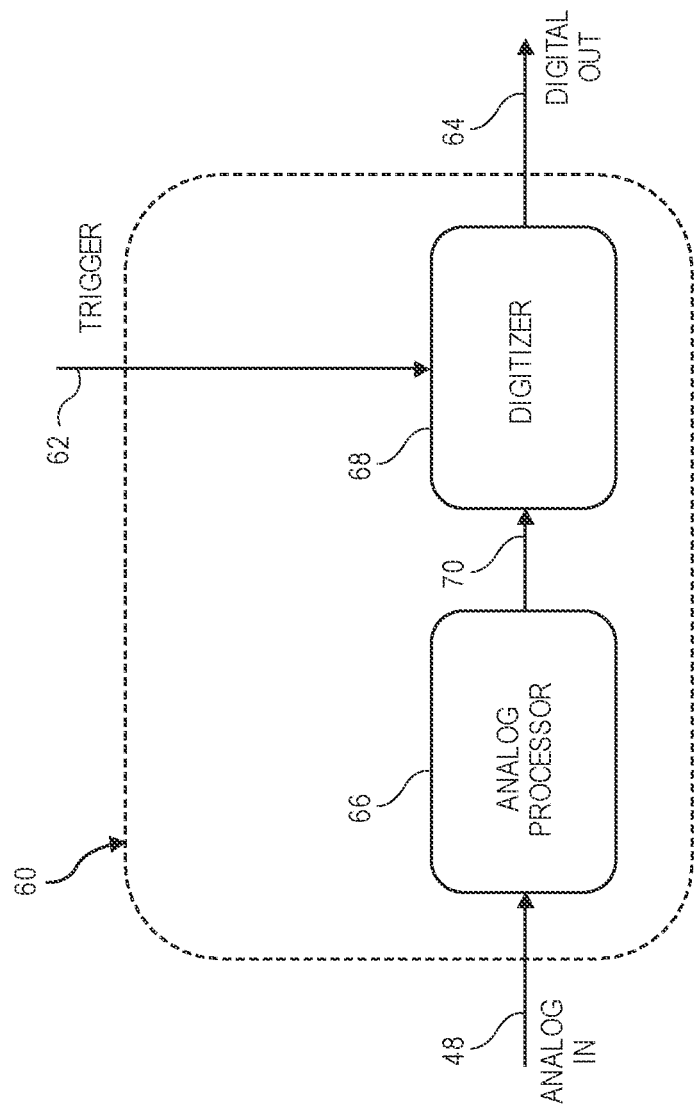
FIG. 12B is a detailed block diagram of the analog processing/digitizing circuitry of FIG. 12A.

Referring to FIG. 12B, a more specific embodiment of the analog processing/digitizing circuitry 60 comprises an analog processor 66 configured for pre conditioning and reducing the TOF profile 48 to a single analog index value 70, and a digitizer 68 (e.g., an analog-to-digital converter (ADC)) configured for digitizing the single analog index value 70 in response to the trigger signal 62 from the controller 24, and outputting the single digitized index value 64 for delivery to the digital portion of the processor 26. Significantly, because the TOF profile 48 is analog processed in this manner prior to digitization (i.e., only one value needs to be digitized), the power requirements and computational overhead can be significantly reduced, thereby reducing the size and cost of the optical measurement system 10. Furthermore, it should be appreciated that the combination of the high-speed detector 36 (e.g., by using an MSM photodiode)(illustrated in FIG. 2) and the analog processing/digitizing circuitry 60, optical measurement system 10 is capable of detecting and processing the signal light 30 in a high-speed manner.

Figure 12C:
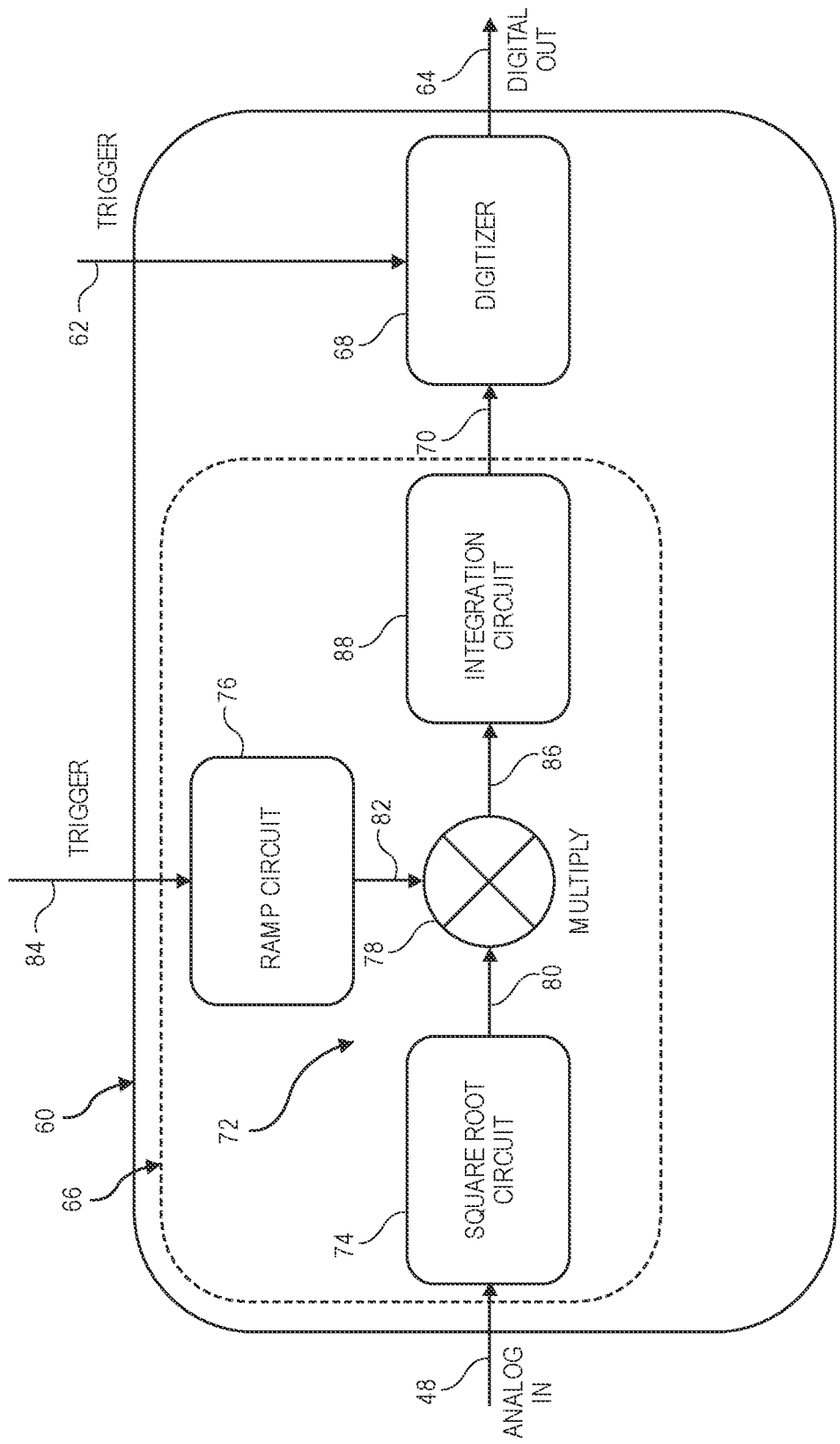
FIG. 12C is an even more detailed block diagram of the analog processing/digitizing circuitry of FIG. 12A.

Referring now to FIG. 12C, the analog processor 66 comprises analog weighting circuitry 72 configured for applying one or more weighting functions to the analog TOF profile 48 of the signal light 30 to increase the CNR of the TOF profile 48. To this end, the weighting circuitry 72 applies the square root weighting function set forth in equation [26] to the TOF profile 48, and in particular, comprises a square root circuit 74 that applies a square root function to the analog TOF profile 48 to equalize the shot noise across the analog TOF profile 48. Alternatively, the weighting function may comprise other fractional powers that decrease the variance of (although not completely equalizing) the shot noise across the analog TOF profile 48. Alternatively, the weighting circuitry 72 may apply a generalized Anscombe Transform function to the analog TOF profile 48 to minimize the variance of the shot noise. In another advantageous embodiment, the weighting circuitry 72 may apply the optimal weighting function set forth in equation [13] to the analog TOF profile 48. The initial application of the square root or other inverse power function, or Anscombe Transform, or optimal weighting function to the analog TOF profile 48 can be considered a pre-conditioning the analog TOF profile 48. As such, the weighting circuitry 72 generates a pre-conditioned TOF profile 80.

In the case where the weighting circuitry 72 applies a square root function (or fractional power) or Anscombe Transform function to the analog TOF profile 48, the weighting circuitry 72 further applies the ramp weighting function set forth in equation [23] to the pre-conditioned TOF profile 80. To this end, the weighting circuitry 72 further comprises a ramp circuit 76 that generates a ramp signal 82 in response to a trigger signal 84 from the controller 24, and analog multiplication circuitry 78 that applies the ramp signal 82 to the pre-conditioned TOF profile 80, and outputs a fully weighted TOF profile 86.

The analog processing/digitizing circuitry 60 is configured for reducing the fully-weighted TOF profile 86 to the single analog index value 70, and in the illustrated embodiment, by computing an area of the fully weighted TOF profile 86. To this end, the analog processing/digitizing circuitry 60 further comprises an analog integration circuit 88 configured for integrating the fully weighted TOF profile 86 to obtain the single analog index value 70 linearly related to the time along the x-axis of the pre-conditioned TOF profile 80 (e.g., approximately 600 ps). In an alternative embodiment, the single analog index value 70 may be normalized by computing an area of the pre-conditioned TOF profile 80 (e.g., via an analog integration circuit (not shown), and dividing the area of the fully weighted TOF profile 86 by the area of the pre-conditioned TOF profile 80.

In essence, the analog processing/digitizing circuitry 60 computes the (normalized or unnormalized) centroid of the pre-conditioned TOF profile 80 in accordance with equation [27] via the ramp weighting function 88. Because neural activity is generally thought to decrease scattering in neuronal tissue, the optical path length 14 becomes incrementally longer and the centroid of a typical TOF profile will be incrementally displaced to the right (i.e., the centroid will increase in time) as the intensity of the fast-optical signal in the optical path 14 decreases. Thus, the single digitized index value 64 output by the digitizer 68 (representing the centroid value) is correlated to the presence and intensity of a fast-optical signal in the optical path 14. As such, the digital portion of the processor 26 is capable of analyzing the single digitized index value 64 to identify one of the two states of the fast-optical signal in the optical path 14. The analog processing/digitizing circuitry 60 can conveniently be fabricated on an integrated circuit to provide efficient on-chip processing.

In alternative embodiments, other types of optical detector assemblies can be used to acquire a TOF profile of the signal light 30, but without the afore-described advantages associated with the high-speed and small form factor TOF measurement hardware of the optical detector assembly 34. For example, a single photon avalanche diode (SPAD)-based technique, swept source OCT-based technique, or the techniques described in U.S. patent application Ser. No. 16/379, 090, entitled "Frequency Domain Optical Spectroscopy For Neural Decoding," and U.S. Provisional patent application Ser. No. 16/392,963, entitled "Interferometric Frequency-Swept Source and Detector in a Photonic Integrated Circuit," can be used to acquire the TOF profile of the signal light 30. In these cases, the processor 26 may acquire a digitized TOF profile of the signal light 30 (with discretized temporal bins) from the optical detector assembly and digitally perform the afore-described pre-conditioning and processing functions (e.g., applying the fractional power to the time bins of the digitized TOF profile and then digitally computing the centroid of the conditioned TOF profile temporal bins), and then determine the presence and intensity of the fast-optical signal in the optical path 14 as described above. To the extent that a Fast-Fourier Transform (FFT) must be used to transform the detected signal light 30 into a digital representation of the TOF profile, such FFT can be performed on, e.g., a field programmable gate array (FPGA), system on a chip (SOC), dedicated IC, or some other digital method.

In one embodiment, different fast-optical intensities respectively correlated to different reference centroid values may be stored in memory in a look-up table format (not shown). The processor 26 may then determine the intensity of the fast-optical signal by matching the digitized centroid value 64 acquired from the analog processing/digitizing circuitry 60 to one of the stored centroid values, and then identifying the fast-optical signal intensity correlated to the matching reference centroid value.

In one embodiment, the optical measurement system 10 may use weighted TOF profiles (either acquired in an analog manner or a digital manner) from two or more optical wavelengths to differentially focus on fast-optical changes in scattering as opposed to hemodynamic changes. Specifically, fast-optical signals that manifest through scattering are expected to obey a different wavelength dependence than hemodynamic absorption-based signals, and thus, it is possible to determine, for instance, linear combinations of measurements at different wavelengths that remove hemodynamic effects while preserving fast-optical scattering effects. For example, absorption-induced changes at optical wavelengths below and above the hemoglobin isobestic point for oxygen may have opposite signs, and thus, sum to zero according to a positively weighted linear combination, whereas scattering induced changes may have the same sign, thus summing constructively under the same linear combination.

In another embodiment, the optical measurement system 10 may perform a calibration procedure by measuring the TOF profile with timed behavioral stimuli. A combination of weighted TOF profiles can be used to maximally discriminate between calibration stimuli. In particular, a set of weights for the TOF profiles can be determined by an iterative optimization method, such as a random search, reinforcement learning, or other technique in order to optimize discrimination of the behavioral stimuli delivered during a calibration phase.

In still another embodiment, the optical measurement system 10 weights TOF profiles from several different source-detector pairs with a Jacobian that describes the sensitivity to cortex-layer scattering changes. This Jacobian can be computed based on simulations of realistic expected geometry.

Figure 13:
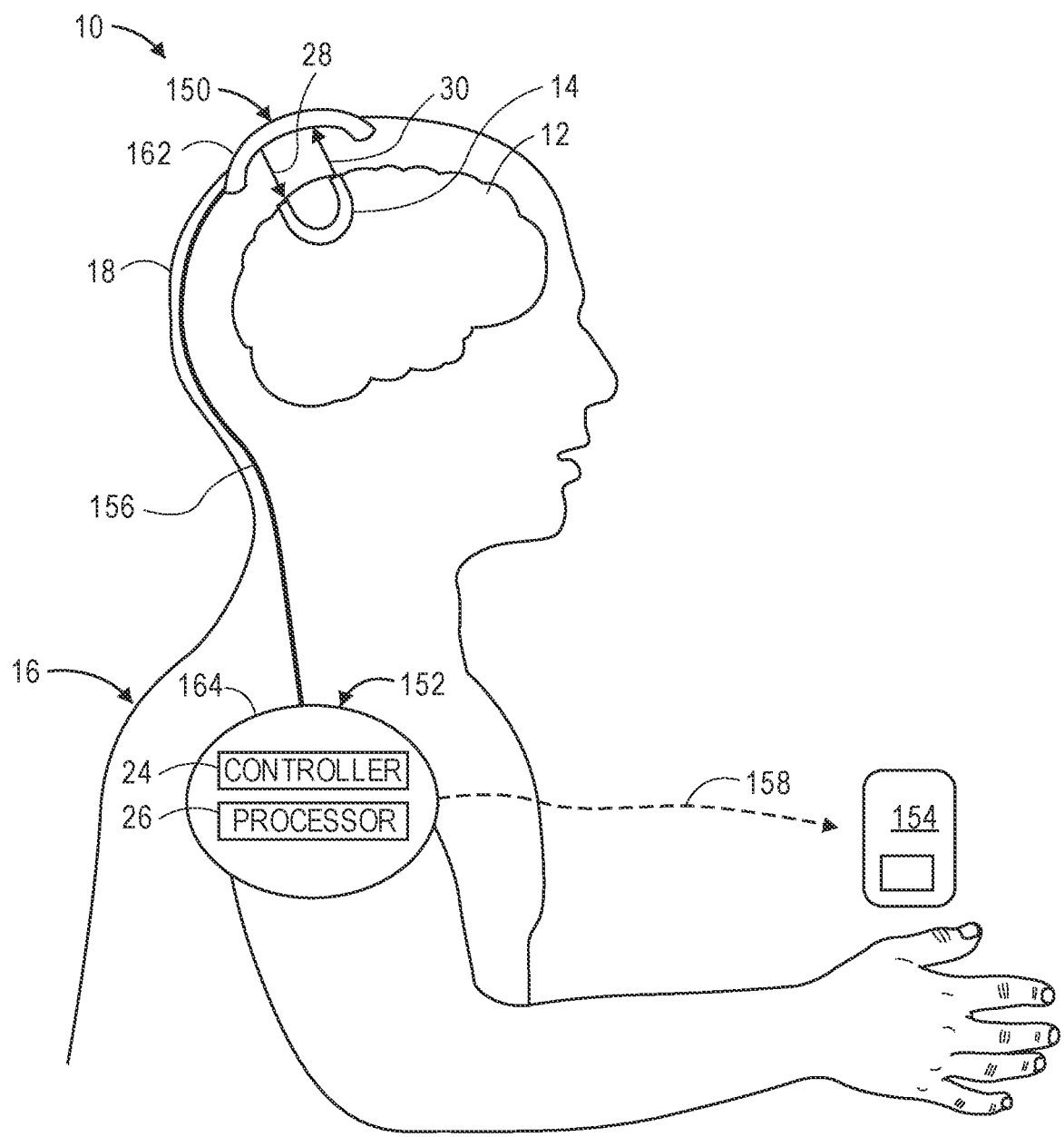
FIG. 13 is a plan view of physical implementation of the optical measurement system of FIG. 1.

Referring now to FIG. 13, the physical implementation of the optical measurement system 10 for use in determining the state of a fast-optical signal in the brain 12 of a user 16 will be described. The optical measurement system 10 includes a wearable unit 150 that is configured for being applied to the user 16, and in this case, worn on the head 18 of the user 16; an auxiliary head-worn or non-head-worn unit 152 (e.g., worn on the neck, shoulders, chest, or arm) coupled to the wearable unit 150 via a wired connection 156 (e.g., electrical wires); and an optional remote processor 154 in communication with the patient-wearable auxiliary unit 152 coupled via a wired connection 158 (e.g., electrical wires). Alternatively, the optical measurement system 10 may use a non-wired connection (e.g., wireless radio frequency (RF) signals (e.g., Bluetooth, Wifi, cellular, magnetic resonance charging, etc.) or optical links (e.g., fiber optic or infrared (IR)) for providing power to or communicating between the respective wearable unit 150 and the auxiliary unit 152, and/or a wired connection between the auxiliary unit 152 and the remote processor 154.

Figure 14:
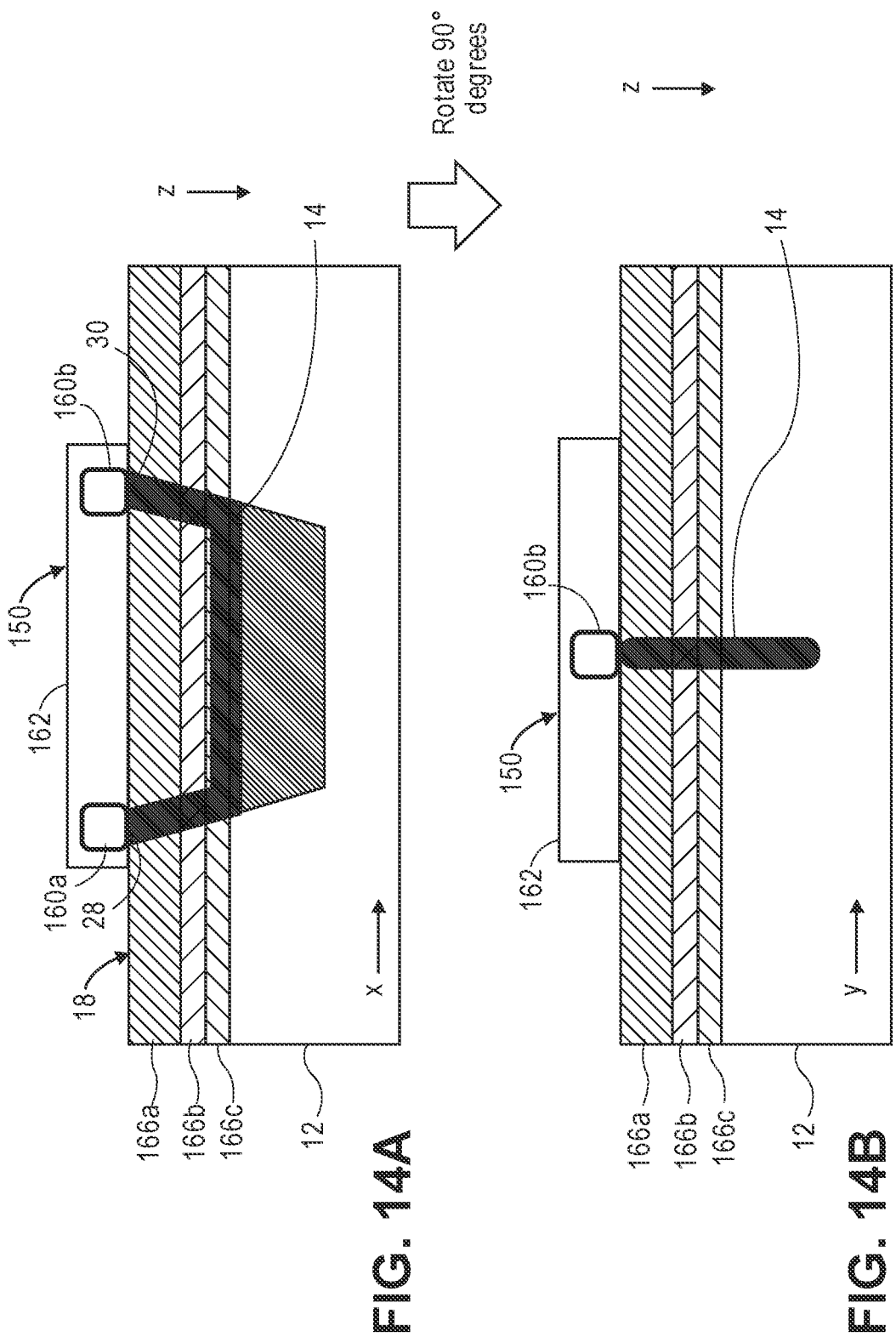
FIG. 14a is one profile view of one arrangement of the output port and input port of the wearable unit of FIG. 13, particularly illustrating the creation of an optical path in tissue between the ports.
FIG. 14b is another profile view of the arrangement of the output port and input port of the wearable unit of FIG. 13.

The wearable unit 150 comprises the optical source assembly 20 and the optical detector assembly 22 (illustrated in FIGS. 1 and 2), and if relevant, the analog processing/digitizing circuitry 60 of the processor 26 (illustrated in FIGS. 12A-12C), an output port 160*a* for emitting the sample light 28 generated by the optical source assembly 20 into the head 18 of the user 16, an input port 160*b* configured for receiving the neural-encoded signal light 40 from the head 18 of the user 16 and delivering it to the optical detector assembly 22, and a support structure 162 containing the optical source assembly 20, optical detector assembly 22, optional analog processing/digitizing circuitry 60, and ports 160*a*, 160*b*. As better illustrated in FIGS. 14A and 14B, the wearable unit 150 is configured for being placed adjacent to the head 18 of the user 16 and emitting the sample light 28 into the brain 12, which is scattered by the brain 12, resulting in the neural-encoded signal light 30 that exits the brain 12. In particular, the sample light 28 first passes through the scalp 166*a*, skull 166, and cerebral spinal fluid (CSF) 166*c* generally along a relatively straight path, enters the brain 12, then exits in reverse fashion along a relatively straight path through the CSF 166*c*, skull 166*b*, and scalp 166*a*, thereby defining a banana-shaped optical path 14. The wearable unit 150 may alternatively, by adding additional optical source-detector pairs, create multiple spatially separated optical paths 14 along which the light may propagate to enable x-y and z-spatial localization of the fast-optical signal.

Referring back to FIG. 13, the support structure 162 may be shaped, e.g., have a banana, headband, cap, helmet, beanie, other hat shape, or other shape adjustable and conformable to the user's head 18, such that the ports 160*a*, 160*b* are in close contact with the outer skin of the head 18, and in this case, the scalp of the user 16. In an alternative embodiment, optical fibers (not shown) may be respectively extended from the ports 160*a*, 160*b*, thereby freeing up the requirement that the ports 160*a*, 160*b* be disposed in close proximity to the surface of the head 18. In any event, an index matching fluid may be used to reduce reflection of the light generated by the wearable unit 150 from the outer skin of the scalp. A locking strap or belt (not shown) can be used to secure the support structure 162 to the head 18 of the user 16.

The auxiliary unit 154 comprises the controller 24 and the processor 26 (illustrated in FIGS. 1 and 2). In the case where wearable unit 150 comprises the analog processing/digitizing circuitry 60 of the processor 26, only the digital circuitry of the processor 26 may be contained in the auxiliary unit 152. The auxiliary unit 152 further comprises a housing 164 containing the controller 24 and processor 26. The controller 24 is configured for controlling the operational functions of the wearable unit 150, whereas the processor 26 is configured for processing the neural-encoded signal light 30 acquired by the wearable unit 150 to distinguish between two states of the fast-optical signal within the brain 12. The auxiliary unit 152 may additionally include a power supply (which if head-worn, may take the form of a rechargeable or non-chargeable battery), a control panel with input/output functions, a display, and memory. Alternatively, power may be provided to the auxiliary unit 152 wirelessly (e.g., by induction). The remote processor 154 may store data from previous sessions, and include a display screen.

Figure 15:
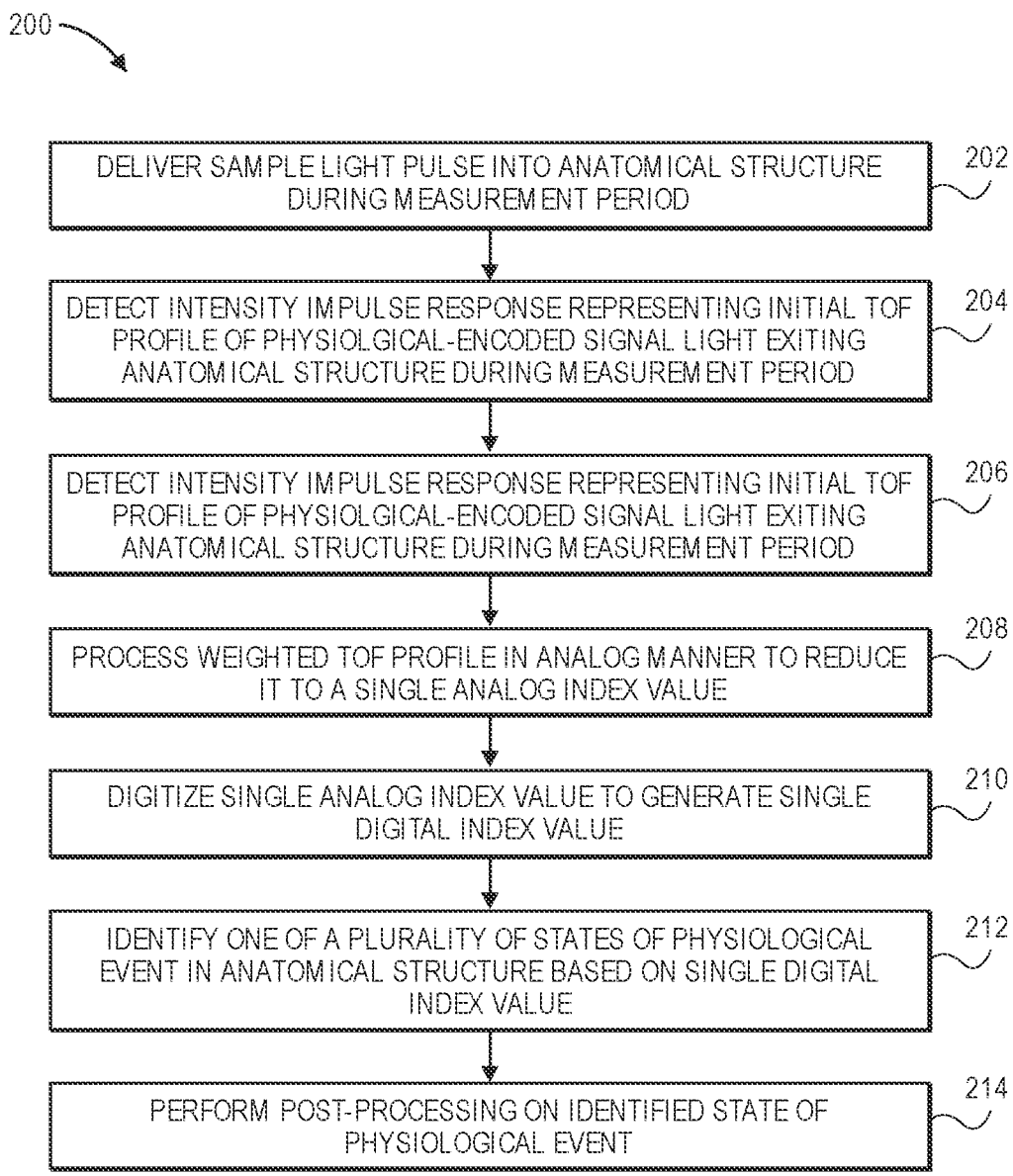
FIG. 15 is a flow diagram illustrating one method used by the optical measurement system of FIG. 1 to non-invasively identify one of plurality of states of a physiological activity in an anatomical structure.

Referring to FIG. 15, having described the structure and function of the optical measurement system 10 (and the variations thereof), one particular method 200 performed by the optical measurement system 10 to non-invasively distinguish between two states (e.g., an active state and inactive states, or two different active states) of a physiological activity (in this case, a fast-optical signal) in the anatomical structure 12 (in this case, the brain 12) will now be described with respect to a single optical source-detector pair, although as described above, multiple optical source-detector pairs may be employed to localize the fast-optical signal in three dimensions in the brain 12. In this method 200, the optical measurement system 10 advantageously employs the variation of the optical detector assembly 22 that directly detects the TOF profile 48 (illustrated in FIG. 3A) and the analog processing/digitizing circuitry 60 (illustrated in FIGS. 12A-12C) that analog processes and digitizes the TOF profile 48.

Prior to the operation of the optical measurement system 10 it is assumed that the optical wavelength(s) of the sample light 28 has been selected to match the physiological activity(s) to be detected in the brain 12. In this case, the physiological activity is a fast-optical signal, in which case, one optical wavelength may be greater than 850 nm. In the case where it is desirable to additionally detect blood oxygen concentration, another optical wavelength may be selected to be in the range of 650 nm to 750 nm.

First, the sample light 28 is delivered along the optical path 14 in the brain 12 during a single measurement period via the optical source assembly 20, such that the sample light 28 is scattered by the brain 12, resulting in the physiological-encoded (neural-encoded) signal light 30 that exits the brain 12 (step 202). In one advantageous embodiment, the sample light 28 takes the form of a single pulse (as illustrated in FIG. 3A). Next, an initial TOF profile 48 of the neural-encoded signal light 30 is directly detected via the optical detector assembly 22 during the measurement period (illustrated in FIGS. 1 and 2) (step 204). In this case where the sample light 28 takes the form of a single pulse, the intensity impulse response representing the initial TOF profile 48 can be detected.

The initial TOF profile 48 is then reduced to a single index value (which is indicative of one of the two states of the fast-optical signal) in an analog manner via the analog processing/digitizing circuitry 60. In particular, one or more weighting functions is applied to the initial TOF profile 48 in an analog manner to create a weighted TOF profile 86 via the weighting circuitry 66 (illustrated in FIG. 12C), such that the weighted TOF profile 86 has a CNR between the two states of the fast-optical signal that is greater than the CNR of the initial TOF profile 48 (step 206), and the weighted TOF profile 86 is processed in an analog manner, e.g., by computing the area of the weighted TOF profile 86 via the integration circuit 88 (illustrated in FIG. 12C) to reduce it to the single analog index value 70 (step 208).

In one embodiment, in accordance with equation [26], one of the weighting functions is a fractional power (e.g., ½) to pre-condition the initial TOF profile 48 to decrease the variance of shot noise across the initial profile 48, thereby generating a pre-conditioned TOF profile 80. Another of the weighting functions comprises a ramp function that is applied to the pre-conditioned TOF profile 80 to generate the fully weighted TOF profile 86. In another embodiment, in accordance with equation [13], the weighting function strictly comprises a change in intensity between two reference TOF profiles respectively corresponding to the two states of the fast-optical signal.

Next, the single analog index value 70 is digitized via the digitizer 68 (illustrated in FIG. 1), thereby generating the single digitized index value 64 (step 210), and the one state of the fast-optical signal is identified based on the single digitized index value 64 via the digital portion of the processor 26 (shown in FIGS. 1 and 2) (step 212). Post-processing can then be performed on the identified state of the fast-optical signal in the brain 12 (step 214), and in the case, such post-processing may comprise determining the level of neural activity within the brain 12 based on the identified state of the fast-optical signal in the brain 12.

Figure 16:
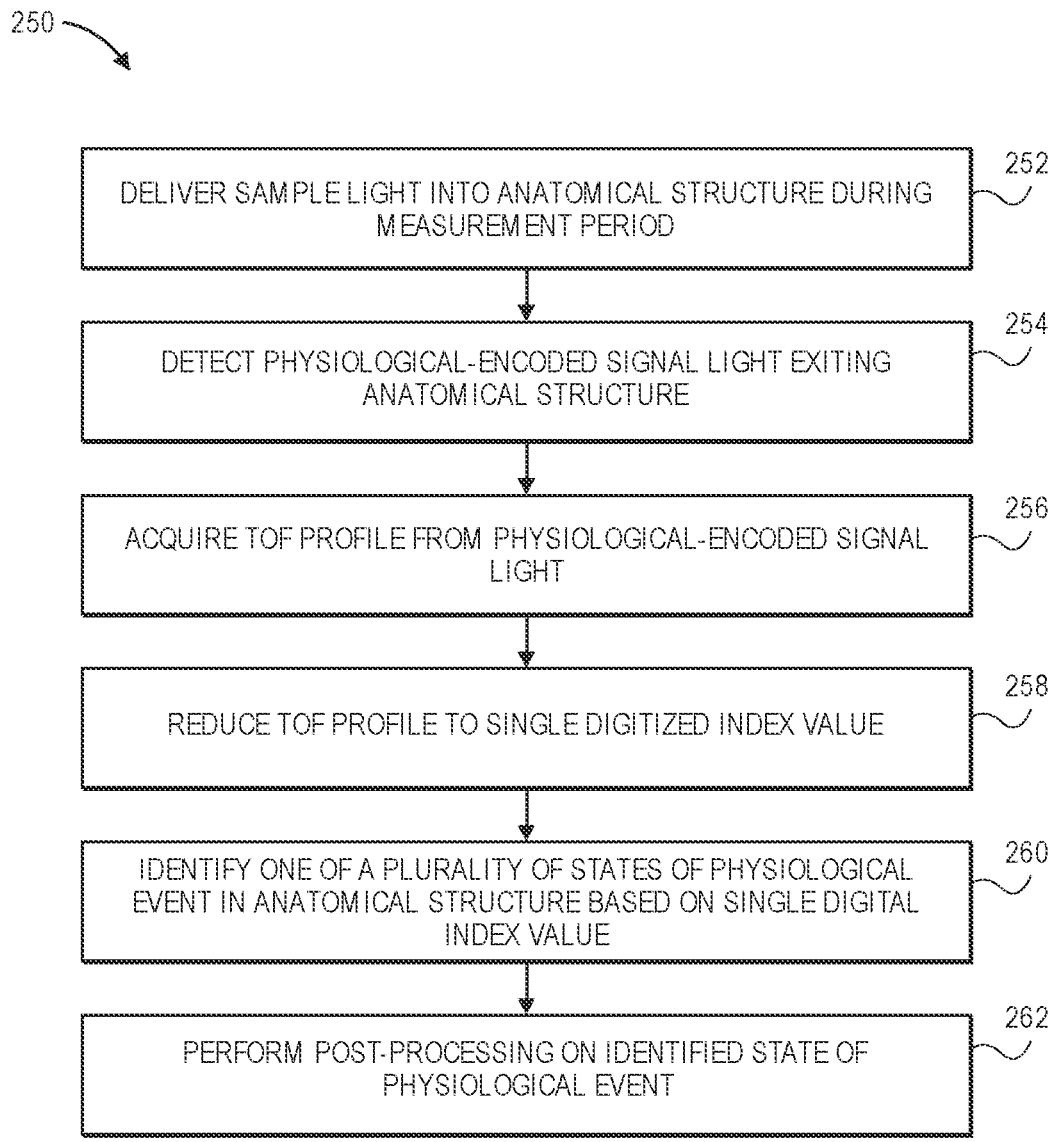
FIG. 16 is a flow diagram illustrating another method used by the optical measurement system of FIG. 1 to non-invasively detecting physiological activity in an anatomical structure.

Referring to FIG. 16, another particular method 250 performed by the optical measurement system 10 to non-invasively distinguish between a plurality of states (e.g., an active state and inactive state, or two different active states) of a physiological activity (in this case, a fast-optical signal) in the anatomical structure 12 (in this case, the brain 12) will now be described. In this method 250, it is assumed that the optical measurement system 10 acquires the TOF profile 48 in any manner (either in an analog and/or digital manner).

First, the sample light 28 is delivered along the optical path 14 in the brain 12 during a single measurement period via the optical source assembly 20, such that the sample light 28 is scattered by the brain 12, resulting in the physiological-encoded (neural-encoded) signal light 30 that exits the brain 12 (step 252). Next, the neural-encoded signal light 30 is detected via the optical detector assembly 22 (illustrated in FIGS. 1 and 2) during the measurement period (step 254), and the TOF profile 48 is acquired from the neural-encoded signal light 30 (step 256). For example, detection of the full intensity impulse response can be employed as described above with respect to steps 202 and 204), or techniques used by SPAD, iNIRS, and others) that yield a digital representation of the intensity impulse response can be employed, or frequency domain measurements that effectively comprise the Fourier transform of such intensity impulse response can be taken, and thus used, via the inverse Fast Fourier transform (IFFT), to reconstruct the intensity impulse response, can be employed.

The TOF profile 48 is then reduced to a single digitized index value 64 (which is indicative of one of the plurality of states of the fast-optical signal) via the processor 26 (step 256). For example, the TOF profile 48 may be pre-conditioned to generate the pre-conditioned TOF profile 80 with decreased shot noise variance (e.g., by applying a fractional power (e.g., ½) to the TOF profile 48), and a centroid of the pre-conditioned TOF profile 80 can be computed in accordance with equation [4] and as performed by the ramp circuit 76, multiplication circuit 78, and integration circuit 88 of FIG. 12C, the active/inactive technique can be applied to the pre-conditioned TOF profile 80 in accordance with equations [5]-[7], or the SVD technique can be applied to the pre-conditioned TOF profile 80 in accordance with equations [8]-[10].

The state of the fast-optical signal is then identified based on the single digitized index value 64 via the processor 26 (shown in FIGS. 1 and 2) (step 258). Post-processing can then be performed on the identified state of the fast-optical signal in the brain 12 (step 260), and in the case, such post-processing may comprise determining the level of neural activity within the brain 12 based on the identified state of the fast-optical signal in the brain 12.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An optical measurement system, comprising:
an optical source configured for delivering sample light in an anatomical structure, such that the sample light is scattered by the anatomical structure, resulting in physiological-encoded signal light that exits the anatomical structure;
an optical detector configured for detecting the physiological-encoded signal light
a processor configured for acquiring an initial time-of-flight (TOF) profile derived from the physiological-encoded signal light, the initial TOF profile having a shot noise variance, the processor further configured for applying a weighting function to the initial TOF profile to generate a weighted TOF profile that has a decreased shot noise variance, the processor further configured for processing the weighted TOF profile by reducing the weighted TOF profile to a single index value indicative of the one state of the physiological activity, and identifying one of a plurality of states of a physiological activity in the anatomical structure based on the single index value.

2. The optical measurement system of claim 1, wherein the plurality of states of the physiological activity comprises an active state and an inactive state.

3. The optical measurement system of claim 1, wherein the plurality of states of the physiological activity comprises two different active states.

4. The optical measurement system of claim 1, wherein the weighting function comprise a fractional power.

5. The optical measurement system of claim 4, wherein the fractional power is ½.

6. The optical measurement system of claim 1, wherein the processor is configured for reducing the weighted TOF profile to the single index value by computing a centroid of the weighted TOF profile.

7. The optical measurement system of claim 1, wherein the processor is configured for reducing the weighted TOF profile to the single index value by computing a dot product of the TOF profile and a reference active TOF profile to yield an active state correlation coefficient $C_a$, computing a dot product of the weighted TOF profile and a reference inactive TOF profile to yield an inactive state correlation coefficient $C_i$, and computing the single index value $\alpha$ in accordance with the equation $$\alpha = \frac{C_a - C_i}{C_a + C_i}.$$

8. The optical measurement system of claim 1, wherein the processor is configured for reducing the TOF profile to the single index value by computing a dot product of the weighted TOF profile and a singular value decomposition of a first reference active TOF profile to yield a first active state correlation coefficient $C_1$, computing a dot product of the weighted TOF profile and a singular value decomposition of a second reference active TOF profile to yield a second active state correlation coefficient $C_2$, and computing the single index value $\alpha$ in accordance with the equation $$\alpha = \frac{C_1 - C_2}{C_1 + C_2}.$$

9. The optical measurement system of claim 1, wherein the optical detector is configured for deriving the initial TOF profile from the physiological-encoded signal light by directly detecting the initial TOF profile of the physiological-encoded signal light, and wherein at least a portion of the processor comprises:
  an analog circuit configured for applying the weighting function to the initial TOF profile to generate the weighted TOF profile, and reducing the weighted TOF profile to the single index value; and
  a digitizer configured for digitizing the single index value;
  wherein at least another portion of the processor is configured for identifying the one state of the physiological activity based on the single digitized index value.

10. The optical measurement system of claim 1, wherein the sample light comprises a single pulse.

11. The optical measurement system of claim 10, wherein the single pulse has an optical pulse width of less than 1 ns.

12. The optical measurement system of claim 10, wherein the single pulse has an optical pulse width of less than 100 ps.

13. The optical measurement system of claim 10, wherein the optical detector comprises a photodiode configured for detecting the physiological-encoded signal light.

14. The optical measurement system of claim 13, wherein the photodiode is one of a metal-semiconductor-metal (MSM) photodiode and a PIN diode.

15. The optical measurement system of claim 1, wherein the optical detector is configured for detecting a frequency domain representation of the physiological-encoded signal light in a frequency domain, wherein the processor is configured for deriving the initial TOF profile from the physiological-encoded signal light by transforming the frequency domain representation of the physiological-encoded signal light into the initial TOF profile.

16. The optical measurement system of claim 1, wherein the anatomical structure is a brain, and wherein the physiological activity is a fast-optical signal.

* * * * *